US 9,039,760 B2

(12) United States Patent
Brady et al.

(10) Patent No.: US 9,039,760 B2
(45) Date of Patent: May 26, 2015

(54) PRE-STRESSED HAPTIC FOR ACCOMMODATING INTRAOCULAR LENS

(71) Applicant: Abbott Medical Optics Inc., Santa Ana, CA (US)

(72) Inventors: Daniel G. Brady, San Juan Capistrano, CA (US); Randall L. Woods, Sun Lakes, AZ (US); Timothy R. Bumbalough, Fullerton, CA (US); Edward P. Geraghty, Rancho Santa Margarita, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/633,688

(22) Filed: Oct. 2, 2012

(65) Prior Publication Data
US 2013/0030525 A1    Jan. 31, 2013

Related U.S. Application Data

(62) Division of application No. 11/618,411, filed on Dec. 29, 2006, now abandoned.

(51) Int. Cl.
*A61F 2/16* (2006.01)
(52) U.S. Cl.
CPC .................................... *A61F 2/1635* (2013.01)
(58) Field of Classification Search
USPC ................. 623/6.11, 6.37–6.4, 6.43
See application file for complete search history.

(56) References Cited

U.S. PATENT DOCUMENTS

| 1,483,509 | A | 5/1921 | Bugbee |
| 2,129,305 | A | 9/1938 | William |
| 2,274,142 | A | 2/1942 | Houchin |
| 2,405,989 | A | 8/1946 | Beach |
| 2,511,517 | A | 6/1950 | Spiegel |
| 2,834,023 | A | 5/1958 | Lieb |
| 3,004,470 | A | 10/1961 | Hans |
| 3,031,927 | A | 5/1962 | Wesley |
| 3,034,403 | A | 5/1962 | Neefe |
| RE25,286 | E | 11/1962 | Carle |
| 3,210,894 | A | 10/1965 | Bentley et al. |
| 3,222,432 | A | 12/1965 | Rene |
| 3,227,507 | A | 1/1966 | William |
| 3,305,294 | A | 2/1967 | Alvarez |

(Continued)

FOREIGN PATENT DOCUMENTS

| AU | 3225789 A1 | 10/1989 |
| CH | 681687 A5 | 5/1993 |

(Continued)

OTHER PUBLICATIONS

English translation of WO93/05733A1.

(Continued)

*Primary Examiner* — Randy Shay
*Assistant Examiner* — Dinah Baria
(74) *Attorney, Agent, or Firm* — Abbott Medical Optics Inc.

(57) ABSTRACT

An intraocular lens is disclosed with an optic that changes shape in response to forces exerted by the zonules of the eye. A haptic with an inner and outer ring couples the optic to the capsular bag of the eye. The haptic stresses the optic when the intraocular lens is in a natural state such that the internal stress is present throughout the accommodation range in order to prevent ripples and/or waves in the optic.

8 Claims, 21 Drawing Sheets

(56) References Cited

U.S. PATENT DOCUMENTS

| | | |
|---|---|---|
| 3,339,997 A | 9/1967 | Wesley |
| 3,415,597 A | 12/1968 | Willard |
| 3,420,006 A | 1/1969 | Barnett |
| 3,431,327 A | 3/1969 | Tsuetaki |
| 3,482,906 A | 12/1969 | Volk |
| 3,507,565 A | 4/1970 | Luis et al. |
| 3,542,461 A | 11/1970 | Girard et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | De Carle |
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |

(56) References Cited

U.S. PATENT DOCUMENTS

| | | |
|---|---|---|
| 4,828,558 A | 5/1989 | Kelman |
| 4,830,481 A | 5/1989 | Futhey et al. |
| 4,834,749 A | 5/1989 | Orlosky |
| 4,840,627 A | 6/1989 | Blumenthal |
| 4,842,601 A | 6/1989 | Smith |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Garabet |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |

(56) References Cited

U.S. PATENT DOCUMENTS

| | | |
|---|---|---|
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 | 5/2001 | Lang et al. |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skotton et al. |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,685,315 B1 | 2/2004 | De Carle |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 | 12/2004 | Willis et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 6,942,695 B1 | 9/2005 | Chapoy et al. |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,344,617 B2 | 3/2008 | Dubrow |
| 7,452,362 B2 | 11/2008 | Zadno-Azizi et al. |

(56) References Cited

U.S. PATENT DOCUMENTS

| | | |
|---|---|---|
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 2001/0001836 A1 | 5/2001 | Cumming |
| 2001/0004708 A1 | 6/2001 | Nagai |
| 2001/0018612 A1 | 8/2001 | Carson et al. |
| 2001/0039451 A1 | 11/2001 | Barnett |
| 2001/0044657 A1 | 11/2001 | Kellan |
| 2002/0004682 A1 | 1/2002 | Zhou et al. |
| 2002/0011167 A1 | 1/2002 | Figov et al. |
| 2002/0072796 A1 | 6/2002 | Hoffmann et al. |
| 2002/0103536 A1 | 8/2002 | Landreville et al. |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0151973 A1 | 10/2002 | Arita et al. |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0020425 A1 | 1/2003 | Ricotti |
| 2003/0033013 A1 | 2/2003 | Callahan et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0105522 A1 | 6/2003 | Glazier |
| 2003/0109925 A1 | 6/2003 | Ghazizadeh et al. |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135272 A1* | 7/2003 | Brady et al. ................ 623/6.37 |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0054408 A1 | 3/2004 | Glick et al. |
| 2004/0082993 A1 | 4/2004 | Woods |
| 2004/0082994 A1 | 4/2004 | Woods et al. |
| 2004/0082995 A1 | 4/2004 | Woods |
| 2004/0106992 A1 | 6/2004 | Lang et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0095127 A1 | 5/2006 | Feingold et al. |
| 2006/0098162 A1 | 5/2006 | Bandhauer et al. |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0209431 A1 | 9/2006 | Spivey |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0032866 A1 | 2/2007 | Portney |
| 2007/0050025 A1 | 3/2007 | Nguyen et al. |
| 2007/0067872 A1 | 3/2007 | Mittendorf et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106379 A1 | 5/2007 | Messner |
| 2007/0106381 A1 | 5/2007 | Blake |
| 2007/0108643 A1 | 5/2007 | Zadno-Azizi et al. |
| 2007/0123591 A1 | 5/2007 | Kuppuswamy et al. |
| 2007/0129798 A1 | 6/2007 | Chawdhary |
| 2007/0135915 A1 | 6/2007 | Klima |
| 2007/0156236 A1 | 7/2007 | Stenger |
| 2007/0213817 A1 | 9/2007 | Esch et al. |
| 2007/0258143 A1 | 11/2007 | Portney |
| 2007/0260309 A1 | 11/2007 | Richardson |
| 2007/0282247 A1 | 12/2007 | Desai et al. |
| 2007/0299487 A1 | 12/2007 | Shadduck |
| 2008/0004699 A1 | 1/2008 | Ben Nun |
| 2008/0125790 A1 | 5/2008 | Tsai et al. |
| 2008/0140192 A1 | 6/2008 | Humayun et al. |
| 2008/0161913 A1 | 7/2008 | Brady et al. |
| 2008/0161914 A1 | 7/2008 | Brady et al. |
| 2008/0300680 A1 | 12/2008 | Joshua |
| 2009/0012609 A1 | 1/2009 | Geraghty et al. |
| 2009/0234448 A1 | 9/2009 | Weeber et al. |
| 2010/0057203 A1 | 3/2010 | Glick et al. |
| 2010/0228346 A1 | 9/2010 | Esch |
| 2011/0035001 A1 | 2/2011 | Woods |
| 2012/0046744 A1 | 2/2012 | Woods et al. |

FOREIGN PATENT DOCUMENTS

| | | |
|---|---|---|
| DE | 2702117 A1 | 7/1978 |
| DE | 3246306 A1 | 6/1984 |
| DE | 4038088 A1 | 6/1992 |
| DE | 19501444 A1 | 7/1996 |
| DE | 19951148 A1 | 4/2001 |
| DE | 20109306 U1 | 8/2001 |
| DE | 10059482 A1 | 6/2002 |
| DE | 10125829 A1 | 11/2002 |
| EP | 64812 A2 | 11/1982 |
| EP | 162573 A2 | 11/1985 |

(56) References Cited

FOREIGN PATENT DOCUMENTS

| | | |
|---|---|---|
| EP | 212616 A2 | 3/1987 |
| EP | 246216 A2 | 11/1987 |
| EP | 328117 A2 | 8/1989 |
| EP | 329981 A1 | 8/1989 |
| EP | 331457 A2 | 9/1989 |
| EP | 336877 A1 | 10/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 478929 A1 | 4/1992 |
| EP | 480748 A1 | 4/1992 |
| EP | 488835 A1 | 6/1992 |
| EP | 492126 A2 | 7/1992 |
| EP | 507292 A1 | 10/1992 |
| EP | 566170 A1 | 10/1993 |
| EP | 601845 A1 | 6/1994 |
| EP | 605841 A1 | 7/1994 |
| EP | 691109 A1 | 1/1996 |
| EP | 766540 A1 | 4/1997 |
| EP | 779063 A1 | 6/1997 |
| EP | 780718 A1 | 6/1997 |
| EP | 897702 A2 | 2/1999 |
| EP | 766540 B1 | 8/1999 |
| EP | 1108402 A2 | 6/2001 |
| EP | 1321112 A1 | 6/2003 |
| EP | 1424049 A1 | 6/2004 |
| EP | 1647241 A2 | 4/2006 |
| EP | 1424049 B1 | 6/2009 |
| FR | 488835 A | 11/1918 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 939016 A | 10/1963 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 0211134 | 1/1990 |
| JP | 2126847 A | 5/1990 |
| JP | H06508279 | 9/1994 |
| JP | 7005399 A2 | 1/1995 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | WO-8404449 A1 | 11/1984 |
| WO | WO8603961 A1 | 7/1986 |
| WO | WO8700299 A1 | 1/1987 |
| WO | WO8707496 A1 | 12/1987 |
| WO | WO-8803961 A1 | 6/1988 |
| WO | WO8902251 A1 | 3/1989 |
| WO | WO8911672 A1 | 11/1989 |
| WO | WO-8911872 A1 | 12/1989 |
| WO | WO9000889 A1 | 2/1990 |
| WO | WO-9109336 A1 | 6/1991 |
| WO | WO-9302639 A1 | 2/1993 |
| WO | WO9305733 A1 | 4/1993 |
| WO | WO9416648 A1 | 8/1994 |
| WO | WO9503783 A1 | 2/1995 |
| WO | WO9610968 A1 | 4/1996 |
| WO | WO9615734 A2 | 5/1996 |
| WO | WO9625126 A1 | 8/1996 |
| WO | WO-9635398 A1 | 11/1996 |
| WO | WO9712272 A1 | 4/1997 |
| WO | WO9727825 A1 | 8/1997 |
| WO | WO9743984 A1 | 11/1997 |
| WO | WO-9805273 A1 | 2/1998 |
| WO | WO-9821621 A1 | 5/1998 |
| WO | WO-9849594 A1 | 11/1998 |
| WO | WO9856315 A1 | 12/1998 |
| WO | WO-9903427 A1 | 1/1999 |
| WO | WO-9907309 A1 | 2/1999 |
| WO | WO-9920206 A1 | 4/1999 |
| WO | WO-9921491 A1 | 5/1999 |
| WO | WO-9929266 A1 | 6/1999 |
| WO | WO-0021467 A1 | 4/2000 |
| WO | WO0027315 A1 | 5/2000 |
| WO | WO-0035379 A1 | 6/2000 |
| WO | WO-0046629 A1 | 8/2000 |
| WO | WO 00/59407 * 10/2000 ................ A61F 2/16 |
| WO | WO0061036 A1 | 10/2000 |
| WO | WO-0066037 A1 | 11/2000 |
| WO | WO0066039 A1 | 11/2000 |
| WO | WO-0066040 A1 | 11/2000 |
| WO | WO-0066041 A1 | 11/2000 |
| WO | WO-0108605 A1 | 2/2001 |
| WO | WO0119288 A1 | 3/2001 |
| WO | WO-0119289 A1 | 3/2001 |
| WO | WO-0128144 A1 | 4/2001 |
| WO | WO-0134061 A1 | 5/2001 |
| WO | WO0134066 A1 | 5/2001 |
| WO | WO0134067 A1 | 5/2001 |
| WO | WO-0156510 A1 | 8/2001 |
| WO | WO-0160286 A1 | 8/2001 |
| WO | WO-0164135 A1 | 9/2001 |
| WO | WO-0164136 A2 | 9/2001 |
| WO | WO-0166042 A1 | 9/2001 |
| WO | WO-0182839 A1 | 11/2001 |
| WO | WO-0189816 A1 | 11/2001 |
| WO | WO-0209620 A2 | 2/2002 |
| WO | WO-0212523 A2 | 2/2002 |
| WO | WO0219949 A2 | 3/2002 |
| WO | WO-02058391 A2 | 7/2002 |
| WO | WO-02071983 A1 | 9/2002 |
| WO | WO-02098328 A1 | 12/2002 |
| WO | WO-03009051 A2 | 1/2003 |
| WO | WO-03015657 A2 | 2/2003 |
| WO | WO03015669 A1 | 2/2003 |
| WO | WO03034949 A2 | 5/2003 |
| WO | WO-03049646 A2 | 6/2003 |
| WO | WO-03057081 A2 | 7/2003 |
| WO | WO-03059196 A2 | 7/2003 |
| WO | WO03059208 A2 | 7/2003 |
| WO | WO03075810 A1 | 9/2003 |
| WO | WO-03084441 A1 | 10/2003 |
| WO | WO-03092552 A1 | 11/2003 |
| WO | WO-2004000171 A1 | 12/2003 |
| WO | WO-2004020549 A1 | 3/2004 |
| WO | WO-2004037127 A2 | 5/2004 |
| WO | WO-2004073559 A1 | 9/2004 |
| WO | WO-2005011531 A2 | 2/2005 |
| WO | WO2005018504 A1 | 3/2005 |
| WO | WO-2005019871 A2 | 3/2005 |
| WO | WO-03082147 A3 | 8/2005 |
| WO | WO-2005084587 A2 | 9/2005 |
| WO | WO2005115278 A1 | 12/2005 |
| WO | WO-2006025726 A1 | 3/2006 |
| WO | WO-2006118452 A1 | 11/2006 |
| WO | WO2007040964 A1 | 4/2007 |
| WO | WO2007067872 A2 | 6/2007 |
| WO | WO-2008077795 A2 | 7/2008 |
| WO | WO-2008079671 A1 | 7/2008 |
| WO | WO-2008108524 A1 | 9/2008 |

(56) References Cited

FOREIGN PATENT DOCUMENTS

| WO | WO-2009021327 A1 | 2/2009 |
|---|---|---|
| WO | WO-2010093823 A2 | 8/2010 |
| ZA | 0888414 | 11/1988 |

OTHER PUBLICATIONS

Fechner P.U., et al., "Iris-Claw Lens in Phakic Eyes to Correct Hyperopia: Preliminary Study," Journal of Cataract and Refractive Surgery, 1998, vol. 24 (1), pp. 48-56.
Mandell R.B., et al., "Mathematical Model of the Corneal Contour," School of Optometry, University of California, Berkeley, pp. 183-197.
U.S. Appl. No. 10/280,918, filed Aug 5, 2003.
U.S. Appl. No. 10/280,937, filed Oct 25, 2005.
U.S. Appl. No. 11/618,325, filed Dec. 29, 2006.
Altan-Yaycioglu R., et al., "Pseudo-accommodation with Intraocular Lenses Implanted in the Bag," Journal of Refractive Surgery, 2002, vol. 18 (3), pp. 271-275.
Chiron, Clemente Optfit Model SP525, Brochure Translation, Jul. 12, 1998.
Cohen A.L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, 1992, vol. 31 (19), pp. 3750-3754.
Contact Lens Practice, 1998, pp. 211, 212, 403, 404, 491 and 792.
English translation of Payer CH681687, May 14, 1993.
European Search Report for Application No. EP09009432, mailed on Aug. 27, 2009, 2 pages.
European Search Report for Application No. EP09178394, mailed on Jan. 25, 2010, 2 pages.
European Search Report for Application No. EP10181797, mailed on Jan. 28, 2011, 2 pages.
European Search Report for Application No. EP11152227, mailed on Oct. 21, 2011, 7 pages.
Extended European Search Report for Application No. EP11152508, mailed on Oct. 25, 2011, 7 pages.
Foldable Intraocular Lens Implants and Small Incision Cataract Surgery, Ohio Valley Eye Physicians, 2004.
Hara T., et al., "Accommodative Intraocular Lens with Spring Action Part 1 Design and Placement in an Excised Animal Eye," Ophthalmic Surgery, 1990, vol. 21 (2), pp. 128-133.
Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
International Preliminary Examination Report for Application No. PCT/US00/11565, mailed on Jun. 12, 2001, 11 pages.
International Preliminary Examination Report for Application No. PCT/US00/11731, mailed on Jul. 27, 2001, 11 pages.
International Preliminary Examination Report for Application No. PCT/US00/24715, mailed on Jan. 11, 2002, 5 pages.
International Preliminary Examination Report for Application No. PCT/US00/24832, mailed on Dec. 11, 2001, 6 pages.
International Preliminary Examination Report for Application No. PCT/US01/07062, mailed on Feb. 20, 2002, 2 pages.
International Preliminary Examination Report for Application No. PCT/US02/14850, mailed on Mar. 20, 2003, 2 pages.
International Preliminary Examination Report for Application No. PCT/US2001/023508, mailed on Oct. 31, 2002, 14 pages.
International Preliminary Examination Report for Application No. PCT/US2002/023908, mailed on Jun. 10, 2003, 3 pages.
International Preliminary Report on Patentability and Written Opinion for Application No. PCT/EP2007/063827, mailed on Oct. 12, 2010, 8 pages.
International Preliminary Report on Patentability and Written Opinion for Application No. PCT/US07/086832, mailed on Jun. 30, 2009, 9 pages.
International Preliminary Report on Patentability and Written Opinion for Application No. PCT/US07/086840, mailed on Aug. 11, 2009, 7 pages.
International Preliminary Report on Patentability and Written Opinion for Application No. PCT/US07/72275, mailed on Jan. 13, 2009, 10 pages.
International Preliminary Report on Patentability and Written Opinion for Application No. PCT/US09/038466, mailed on Sep. 28, 2010, 7 pages.
International Preliminary Report on Patentability and Written Opinion for Application No. PCT/US2004/29704, mailed on Mar. 13, 2006, 8 pages.
International Preliminary Report on Patentability and Written Opinion for Application No. PCT/US2004/41839, mailed on Jun. 20, 2006, 4 pages.
International Preliminary Report on Patentability and Written Opinion for Application No. PCT/US2006/036242, mailed on Apr. 1, 2008, 10 pages.
International Preliminary Report on Patentability and Written Opinion for Application No. PCT/US2006/41500, mailed on Apr. 29, 2008, 9 pages.
International Preliminary Report on Patentability and Written Opinion for Application No. PCT/US2006/61671, mailed on Jul. 1, 2008, 7 pages.
International Preliminary Report on Patentability and Written Opinion for Application No. PCT/US2007/089060, mailed on Aug. 30, 2011, 7 pages.
International Preliminary Report on Patentability and Written Opinion for Application No. PCT/US2010/039858, mailed on Jan. 4, 2012, 11 pages.
International Preliminary Report on Patentability and Written Opinion for Application No. PCT/US2010/039860, mailed on Jan. 4, 2012, 10 pages.
International Preliminary Report on Patentability and Written Opinion for Application No. PCT/US2010/044248, mailed on Feb. 7, 2012, 6 pages.
International Preliminary Report on Patentability and Written Opinion for Application No. PCT/US2010/047011, mailed on Feb. 28, 2012, 9 pages.
International Preliminary Report on Patentability for Application No. PCT/US2007/060112, mailed on Jul. 15, 2008, 1 page.
International Search Report and Written Opinion for Application No. PCT/US2010/023946, mailed on Feb. 22, 2011, 10 pages.
International Search Report for Application No. PCT/EP2007/063827, mailed on Oct. 5, 2010, 5 pages.
International Search Report for Application No. PCT/US00/11565, mailed on Sep. 8, 2000, 3 pages.
International Search Report for Application No. PCT/US00/11731, mailed on Aug. 21, 2000, 3 pages.
International Search Report for Application No. PCT/US00/24715, mailed on Feb. 27, 2001, 3 pages.
International Search Report for Application No. PCT/US00/24832, mailed on Dec. 12, 2000, 2 pages.
International Search Report for Application No. PCT/US01/07062, mailed on Aug. 24, 2001, 3 pages.
International Search Report for Application No. PCT/US01/23508, mailed on Jan. 15, 2002, 3 pages.
International Search Report for Application No. PCT/US02/14850, mailed on Aug. 12, 2002, 2 pages.
International Search Report for Application No. PCT/US07/086832, mailed on Sep. 11, 2008, 4 pages.
International Search Report for Application No. PCT/US07/086840, mailed on Jul. 27, 2009, 3 pages.
International Search Report for Application No. PCT/US07/72275, mailed on Sep. 9, 2008, 6 pages.
International Search Report for Application No. PCT/US09/038466, mailed on Sep. 17, 2009, 2 pages.
International Search Report for Application No. PCT/US2002/023908, mailed on Apr. 15, 2003, 1 page.

(56) References Cited

OTHER PUBLICATIONS

International Search Report for Application No. PCT/US2002/39428, mailed on Aug. 19, 2003, 5 pages.
International Search Report for Application No. PCT/US2003/01268, mailed on Nov. 3, 2003, 4 pages.
International Search Report for Application No. PCT/US2003/01270, mailed on Jun. 25, 2003, 5 pages.
International Search Report for Application No. PCT/US2003/34163, mailed on Apr. 12, 2004, 1 page.
International Search Report for Application No. PCT/US2003/34167, mailed on Sep. 2, 2004, 1 page.
International Search Report for Application No. PCT/US2004/29704, mailed on Jan. 25, 2005, 3 pages.
International Search Report for Application No. PCT/US2004/41839, mailed on May 11, 2005, 1 page.
International Search Report for Application No. PCT/US2006/36242, mailed on Feb. 7, 2007, 4 pages.
International Search Report for Application No. PCT/US2006/41500, mailed on Aug. 23, 2007, 5 pages.
International Search Report for Application No. PCT/US2006/61671, mailed on Apr. 5, 2007, 3 pages.
International Search Report for Application No. PCT/US2007/060112, mailed on Jun. 15, 2007, 2 pages.
International Search Report for Application No. PCT/US2007/089060, mailed on Apr. 24, 2008, 3 pages.
International Search Report for Application No. PCT/US2010/039858, mailed on Jan. 20, 2011, 3 pages.
International Search Report for Application No. PCT/US2010/039860, mailed on Dec. 14, 2010, 6 pages.
International Search Report for Application No. PCT/US2010/044248, mailed on Nov. 4, 2010, 4 pages.
International Search Report for Application No. PCT/US2010/047011, mailed on Feb. 16, 2011, 7 pages.
International Search Report for Application No. PCT/US99/26368, mailed on Apr. 11, 2000, 3 pages.
International Search Report for Application No. PCT/US99/29097, mailed on Apr. 14, 2000, 6 pages.
International Search Report for U.S. Application No. PCT/US2006/030606, mailed on Dec. 1, 2006, 3 pages.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
JP2126847A—English Translation, May 15, 1990.
Klien S.A., "Understanding the Diffractive Bifocal Contact Lens," Optometry and Vision Science, 1993, vol. 70 (6), pp. 439-460.
Mandell R.B., "Contact Lens Practice", 4th Edition, Charles C. Thomas Publishers, 1988, 11 pages.
Marron J.C., et al., "Higher-order Kinoforms," Computer and Optically Formed Holographic Optics, 1990, vol. 1211, pp. 62-66.
McCarey B.E., et al., "Modeling Glucose Distribution In The Cornea," Current Eye Research, 1990, vol. 9 (11), pp. 1025-1039.
Office Action mailed Jul. 19, 2011 for Japanese Application No. 2006526344 filed Sep. 10, 2004.
Partial International Search Report for Application No. PCT/US2010/039858, mailed on Oct. 5, 2010, 2 pages.
Pending Claims mailed Jul. 29, 2009 for U.S. Appl. No. 11/618,411, filed Dec. 29, 2006.
Prosecution History for U.S. Appl. No. 10/958,871 (US20050234547) filed Oct. 5, 2004.
Prosecution History for U.S. Appl. No. 11/057,705 (US20060184244) filed Feb. 14, 2005.
Prosecution History for U.S. Appl. No. 11/195,422 (US20050267575) filed Aug. 1, 2005.
Prosecution History for U.S. Appl. No. 11/426,888, filed Jun. 27, 2006.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Simonov A.N., et al., "Cubic Optical Elements for an Accommodative Intraocular Lens," Optics Express, 2006, vol. 14 (17), pp. 7757-7775.
Supplementary European Search Report for Application No. EP00980998, mailed on Sep. 11, 2007, 2 pages.
Supplementary European Search Report for Application No. EP02748257, mailed on Jun. 23, 2008, 2 pages.
Supplementary European Search Report for Application No. EP03777934, mailed on Jan. 26, 2010, 3 pages.
Supplementary European Search Report for Application No. EP03809651, mailed on Aug. 11, 2006, 2 pages.
Supplementary European Search Report for Application No. EP04814069, mailed on Jul. 12, 2007, 1 page.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Written Opinion for Application No. PCT/US2007/060112, mailed on Jun. 15, 2007, 6 pages.
Amo Specs Model AC-21B, 1992.
English translation of WO93/05733A1, Jan. 4, 1993.
Fechner P.U., et al., "Iris-Claw Lens In Phakic Eyes To Correct Hyperopia: Preliminary Study," Journal of Cataract and Refractive Surgery, 1998, vol. 24 (1), pp. 48-56.
Mandell R.B., et al., "Mathematical Model of the Corneal Contour," School of Optometry, University of California, Berkeley, pp. 183-197, 1971.
Menezo J.L., et al., "Endothelial Study of Iris-Claw Phakic Lens: Four Year Follow-Up," Journal of Cataract Refractive Surgery, 1998, vol. 24 (8), pp. 1039-1049.
U.S. Appl. No. 11/966,365—Pending claims submitted on Dec. 28, 2007.
U.S. Appl. No. 09/656,661, filed Sep. 7, 2000.
Study Design of Nuvita, Mar. 20, 1997, 5 pages.
Thornton S., "Accommodation in Pseudophakia," 1991, pp. 159-162.
U.S. Appl. No. 10/280,918, filed Aug. 5, 2003.
U.S. Appl. No. 10/280,937, filed Oct. 25, 2005.
U.S. Appl. No. 09/721,072, filed Nov. 22, 2000.
U.S. Appl. No. 11/618,325, filed Dec. 29, 2006 (Brady et al).

* cited by examiner

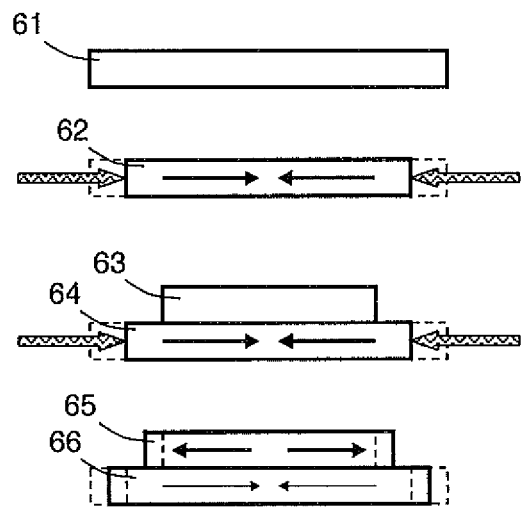
Fig. 6
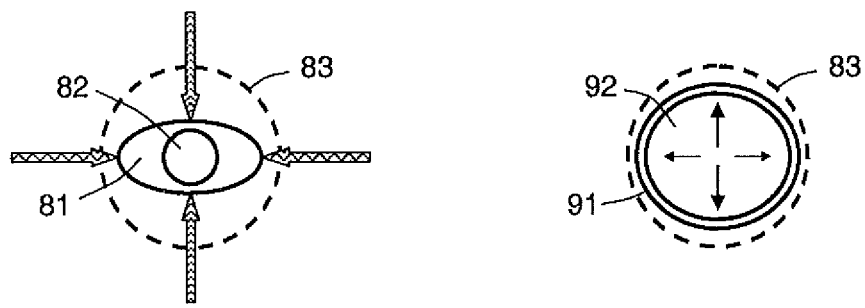
Fig. 8                    Fig. 9

PRE-STRESSED HAPTIC FOR ACCOMMODATING INTRAOCULAR LENS

RELATED APPLICATIONS

This application is a divisional application and claims priority to U.S. application Ser. No. 11/618,411 filed on Dec. 29, 2006, the entire contents of which are hereby incorporated by reference in their entirety for all purposes as if fully set forth herein.

BACKGROUND OF THE INVENTION

1. Field of the Invention

The present invention is directed to intraocular lenses, and more particularly to accommodating intraocular lenses.

2. Description of the Related Art

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange.

The simplest IOLs have a single focal length, or, equivalently, a single power. Unlike the eye's natural lens, which can adjust its focal length within a particular range in a process known as accommodation, these single focal length IOLs cannot generally accommodate. As a result, objects at a particular position away from the eye appear in focus, while objects at an increasing distance away from that position appear increasingly blurred.

An improvement over the single focal length IOLs is an accommodating IOL, which can adjust its power within a particular range. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accommodation range or add power is defined as the near power minus the far power. In general, an accommodation range of 2 to 4 diopters is considered sufficient for most patients.

The human eye contains a structure known as the capsular bag, which surrounds the natural lens. The capsular bag is transparent, and serves to hold the lens. In the natural eye, accommodation is initiated by the ciliary muscle and a series of zonular fibers, also known as zonules. The zonules are located in a relatively thick band mostly around the equator of the lens, and impart a largely radial force to the capsular bag that can alter the shape and/or the location of the natural lens and thereby change its effective power.

In a typical surgery in which the natural lens is removed from the eye, the lens material is typically broken up and vacuumed out of the eye, but the capsular bag is left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which refracts light that passes through it and forms an image on the retina, and a haptic, which mechanically couples the optic to the capsular bag. During accommodation, the zonules exert a force on the capsular bag, which in turn exerts a force on the optic. The force may be transmitted from the capsular bag directly to the optic, or from the capsular bag through the haptic to the optic.

A desirable optic for an accommodating IOL is one that distorts in response to a squeezing or expanding radial force applied largely to the equator of the optic (i.e., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

One challenge in implementing such an optic is designing the optic so that it does not distort undesirably anywhere in the accommodation range. More specifically, while a change in surface curvature may be desirable for causing a change in optical power, irregularities on one or both surfaces of the optic may undesirably lead to optical aberrations or artifacts and thereby degrade the performance of the optic.

Accordingly, there exists a need for an intraocular lens having an optic with an increased resistance to undesirable surface irregularities during accommodation.

SUMMARY OF THE INVENTION

An embodiment is an intraocular lens for implantation into a capsular bag of an eye, comprising a stressed optic; and a haptic for coupling the optic to the capsular bag. The haptic stresses the stressed optic when the intraocular lens is in a natural state.

A further embodiment is an intraocular lens for implantation into a capsular bag of an eye, comprising an optic; and a haptic for coupling the optic to the capsular bag. The optic is under tension when the intraocular lens is in a natural state.

A further embodiment is an intraocular lens for implantation into a capsular bag of an eye, comprising an optic having a periphery; and an annular ring engaging at least a portion of the periphery of the optic for coupling the optic to the capsular bag. The annular ring stresses the optic in the absence of an external compressive force on the annular ring.

A further embodiment is an intraocular lens for implantation into a capsular bag of an eye, comprising an optic having a periphery; and an annular ring engaging at least a portion of the periphery of the optic for coupling the optic to the capsular bag. The optic has a uncompressed surface profile in the absence of an external compressive force on the annular ring. The optic has a compressed surface profile in the presence of an external compressive force on the annular ring. The compressed surface profile is more spherical than the uncompressed surface profile.

A further embodiment is an intraocular lens for implantation into a capsular bag of an eye, comprising an optic having an equatorial region and a shape, the shape comprising an anterior curvature and a posterior curvature; and a haptic for coupling the optic to the capsular bag. The optic can change its shape in response to essentially radial forces exerted by the capsular bag and transmitted to the equatorial region of the optic by the haptic. The haptic is stiffer than the optic. The haptic is coaxial with the optic. The haptic stresses the optic when the intraocular lens is in a natural state.

A further embodiment is a method for manufacturing an intraocular lens having a haptic, comprising stressing the haptic under an external stress; placing an optic within the haptic; and removing the external stress from the haptic, so that at equilibrium, the optic is internally stressed.

BRIEF DESCRIPTION OF THE DRAWINGS

FIG. 6 is an end-on drawing of a haptic and optic, shown throughout various stages of construction.

FIG. 8 is a schematic drawing of an optic and a haptic under compression from an asymmetric external force.

FIG. 9 is a schematic drawing of the haptic and optic of FIG. 8 removed from the asymmetric external force.

DETAILED DESCRIPTION OF THE DRAWINGS

In a healthy human eye, the natural lens is housed in a structure known as the capsular bag. The capsular bag is driven by a ciliary muscle and zonular fibers (also known as zonules) in the eye, which can compress and/or pull on the capsular bag to change its shape. The motions of the capsular bag distort the natural lens in order to change its power and/or the location of the lens, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the ciliary muscle and/or zonules, it is desirable that the implanted intraocular lens change its power and/or location in the eye in a manner similar to that of the natural lens. Such an accommodating lens may produce improved vision over a lens with a fixed power and location that does not accommodate.

Figure 1:
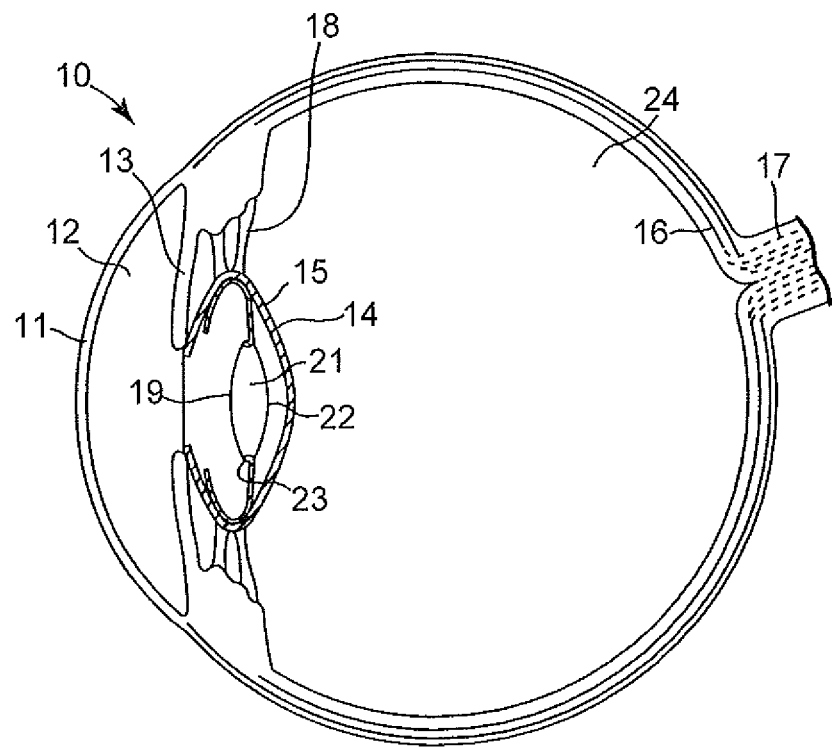
FIG. 1 is a cross-section drawing of a human eye with an implanted intraocular lens, focused on a relatively close object.

FIG. 1 shows a human eye 10, after an accommodating intraocular lens has been implanted. Light enters from the left of FIG. 1, and passes through the cornea 11, the anterior chamber 12, the iris 13, and enters the capsular bag 14. Prior to surgery, the natural lens occupies essentially the entire interior of the capsular bag 14. After surgery, the capsular bag 14 houses the intraocular lens, in addition to a fluid that occupies the remaining volume and equalizes the pressure in the eye. The intraocular lens is described in more detail below. After passing through the intraocular lens, light exits the posterior wall 15 of the capsular bag 14, passes through the posterior chamber 24, and strikes the retina 16, which detects the light and converts it to a signal transmitted through the optic nerve 17 to the brain.

A well-corrected eye forms an image at the retina 16. If the lens has too much or too little power, the image shifts axially along the optical axis away from the retina, toward or away from the lens. Note that the power required to focus on a close or near object is more than the power required to focus on a distant or far object. The difference between the "near" and "far" powers is known typically as the add power or the range of accommodation. A normal range of accommodation is about 3 to 4 diopters, which is considered sufficient for most patients.

The capsular bag is acted upon by the ciliary muscle 25 via the zonules 18, which distort the capsular bag 14 by stretching it radially in a relatively thick band about its equator. Experimentally, it is found that the ciliary muscle 25 and/or the zonules 18 typically exert a total ocular force of up to about 10 grams of force, which is distributed generally uniformly around the equator of the capsular bag 14. Although the range of ocular force may vary from patient to patient, it should be noted that for each patient, the range of accommodation is limited by the total ocular force that can be exert. Therefore, it is highly desirable that the intraocular lens be configured to vary its power over the full range of accommodation, in response to this limited range of ocular forces. In other words, it is desirable to have a relatively large change in power for a relatively small driving force.

Because the zonules' or ocular force is limited, it is desirable to use a fairly thin lens, compared to the full thickness of the capsular bag. In general, a thin lens may distort more easily than a very thick one, and may therefore convert the ocular force more efficiently into a change in power. In other words, for a relatively thin lens, a lower force is required to cover the full range of accommodation.

Note that the lens may be designed so that its relaxed state is the "far" condition (sometimes referred to as "disaccommodative biased"), the "near" condition ("accommodative biased"), or some condition in between the two.

The intraocular lens itself generally has two components: an optic 21, which is made of a transparent, deformable and/or elastic material, and a haptic 23, which holds the optic 21 in place and mechanically transfers forces on the capsular bag 14 to the optic 21. The haptic 23 may have an engagement member with a central recess that is sized to receive the peripheral edge of the optic 21.

When the eye 10 focuses on a relatively close object, as shown in FIG. 1, the zonules 18 relax and compress the capsular bag 14 returns to its natural shape in which it is relatively thick at its center and has more steeply curved sides. As a result of this action, the power of the lens increases (i.e., one or both of the radii of curvature can decrease, and/or the lens can become thicker, and/or the lens may also move axially), placing the image of the relatively close object at the retina 16. Note that if the lens could not accommodate, the image of the relatively close object would be located behind the retina, and would appear blurred.

Figure 2:
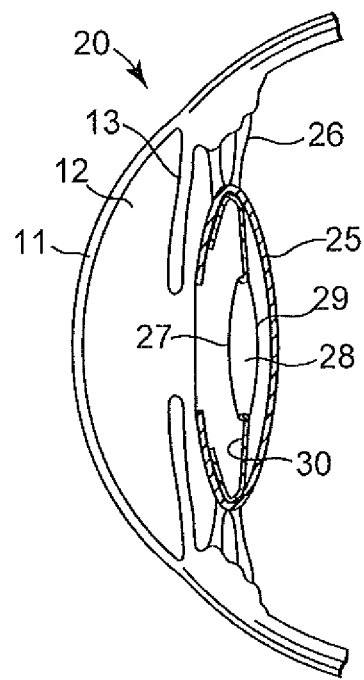
FIG. 2 is a cross-section drawing of a portion of a human eye with an implanted intraocular lens, focused on a relatively distant object.

FIG. 2 shows a portion of an eye 20 that is focused on a relatively distant object. The cornea 11 and anterior chamber 12 are typically unaffected by accommodation, and are substantially identical to the corresponding elements in FIG. 1. To focus on the distant object, the ciliary muscle 37 contracts and the zonules 26 retract and change the shape of the capsular bag 25, which becomes thinner at its center and has less steeply curved sides. This reduces the lens power by flattening (i.e., lengthening radii of curvature and/or thinning) the lens, placing the image of the relatively distant object at the retina (not shown).

For both the "near" case of FIG. 1 and the "far" case of FIG. 2, the intraocular lens itself deforms and changes in response to the ciliary muscles and/or to the distortion of the capsular bag. For the "near" object, the haptic 23 compresses the optic 21 at its edge, increasing the thickness of the optic 21 at its center and more steeply curving its anterior face 19 and/or its posterior face 22. As a result, the lens power increases. For the "far" object, the haptic 30 expands, pulling on the optic 28 at its edge, and thereby decreasing the thickness of the optic 28 at its center and less steeply curving (e.g., lengthening one or both radius of curvature) its anterior face 27 and/or its posterior face 29. As a result, the lens power decreases.

Note that the specific degrees of change in curvature of the anterior and posterior faces depend on the nominal curvatures. Although the optics 21 and 28 are drawn as bi-convex, they may also be plano-convex, meniscus or other lens shapes. In all of these cases, the optic is compressed or expanded by forces applied by the haptic to the edge and/or faces of the optic. In addition, there may be some axial movement of the optic. In some embodiments, the haptic is configured to transfer the generally symmetric radial forces symmetrically to the optic to deform the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optic may optionally have one or more diffractive elements, one or more multifocal elements, and/or one or more aspheric elements.

In many cases, it is desirable that during accommodation, the distortion of the optic produces a change in optic thickness and/or a change in the radius of curvature of the anterior and/or posterior surfaces of the optic. Any other types of distortions to the surface, such as "ripples" or "waves", may unacceptably degrade the optical performance of the lens. These "ripples" or "waves" are described in more detail below.

Because the optic is round, it may be difficult to envision any undesirable surface ripples that may accompany a squeezing or expanding of the optic about its equator. For this reason, it is instructive to consider the geometry of a linear beam or rod, which can produce analogous ripples along a single dimension. This 1-D geometry is much simpler to visualize, and adequately describes the issue of undesirable surface distortion.

Consider a linear beam or rod, which is being compressed by pushing on its ends. While the intended effect of the compression may be to shorten the beam and/or produce a slight bulge along the length of the beam, an unintended effect may be to cause a small amount of "buckling" along the length of the beam. Similarly, if the beam is stretched by pulling on its ends, the intended effect of the stretching may be to lengthen the beam and/or produce a slight thinning of the beam along its length, but an unintended effect may be to cause a small amount of "cracking" along the surface, similar in character to that of a desert floor. Both the "buckling" and "cracking" may occur along the surface of the beam, while the compression or expansion may be initiated at or near the ends of the beam.

This analogy may be extended to the two-dimensional, essentially circular geometry of the accommodating optic. To focus on relatively near objects, as in FIG. 1, the haptic may squeeze the optic about its equator and cause a radial compression of the optic. The intended effect of the squeezing may be to increase the thickness of the optic and/or change the curvature of the anterior and/or posterior surfaces of the optic. However, an unintended effect may be to produce the two-dimensional, circular equivalent of "buckling" on one or both of these surfaces. Similarly, to focus on relatively distant objects, as in FIG. 2, the haptic may stretch the optic about its equator and cause a radial expansion of the optic. The intended effect of the expansion may be to decrease the thickness of the optic and/or change the curvature of the anterior and/or posterior surfaces of the optic. However, an unintended effect may be to produce the two-dimensional, circular equivalent of "cracking" on one or both of these surfaces. For the purposes of this document, the circular equivalents of "buckling" and "cracking" may be referred to as "ripples" or "waves". For known optics, these "ripples" or "waves" may degrade the performance of the optic, which is highly undesirable.

It is possible that the "ripples" or "waves" during accommodation may be avoided if the optic has internal stress. For instance, if the haptic applies a compression or expansion force to the optic, separate and distinct from any compression or expansion forces applied by the capsular bag of the eye, then the optic may have some internal stress, which may reduce any "ripples" or "waves" that appear during accommodation. The internal stress in the optic may be present throughout the range of accommodation, or may alternatively pass through "zero" at some point in the range of accommodation.

In some embodiments, the anterior and/or posterior surfaces may be designed so that they attain particular profiles when the optic is compressed about its equator, as occurs when the lens is implanted. For instance, in some embodiments, it may be particularly desirable to have spherical anterior and/or posterior surfaces; in these embodiments, the anterior and/or posterior surface profiles may or may not deviate from spherical when the optic is uncompressed about its equator. In other words, for some embodiments, compressing the optic about its equator causes the anterior and/or posterior surfaces to become more spherical in profile. If there is asphericity in either surface in the uncompressed state, it may be reduced when the optic is compressed.

Figure 3:
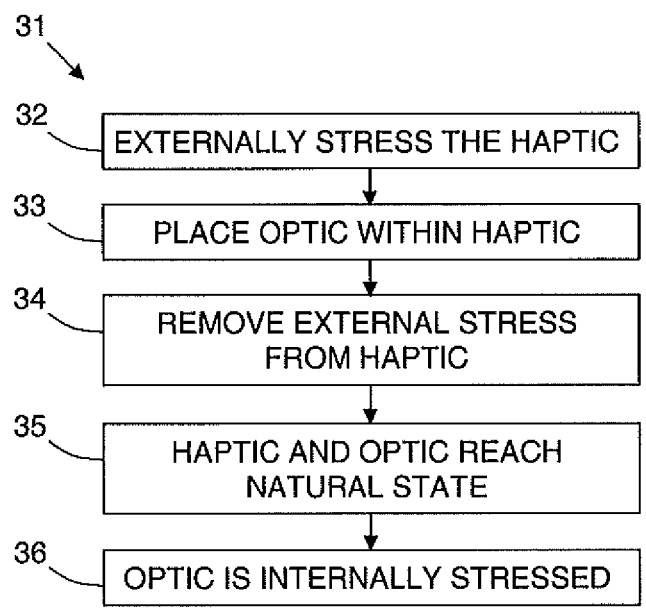
FIG. 3 is a flow chart of a manufacturing process that may induce an internal stress to the optic.

FIG. 3 is a flow chart of a manufacturing process 31 that may induce an internal stress to the optic when the intraocular lens is in a natural or nominally unstressed state.

First, externally stress the haptic, as in element 32. In some embodiments, an external compressive or expansive force is applied to a haptic, so that the haptic becomes compressed or stretched. Note that the haptic may be made from a generally elastic material, so that the haptic may return roughly to its initial shape and size when the external force is removed.

Next, place or form an optic within the externally stressed haptic, as in element 33. In some embodiments, the optic may be molded or otherwise manufactured directly onto the externally stressed haptic. In other embodiments, the optic may be manufactured separately, then attached to the haptic. For the purposes of this document, for all of these embodiments, the optic is said to be "placed" within the haptic.

In some embodiments, the optic is held by the haptic in a region around the equator of the optic. The haptic may contact the optic at the edge of the optic, at the circumference of the anterior face of the optic, and/or at the circumference of the posterior face of the optic. The haptic may optionally extend over a portion of the anterior and/or posterior faces, typically around the edge of the optic and outside the clear aperture of the optic. In some embodiments, the haptic may not truly surround the optic, but may contact it in portions at or near the equator of the optic or may contact it only on the anterior or posterior face. In other embodiments, portions of the haptic may be disposed inside the optic so that the haptic portion protrudes into the optic. For the purposes of this document, the optic is said to be placed "within" the haptic for all of these orientations.

Next, remove the external stress from the haptic, as in element 34. This may involve removing the external compressive or expansive force applied in element 32.

The intraocular lens reaches a natural state, as in element 35. For the purposes of this document, a "natural" state is a state of the intraocular lens in which there is an absence of external forces, such as external compressive or expansive forces applied in element 32. In some embodiments, the "natural" state is the state of the intraocular lens prior to implantation into an eye.

Finally, the optic is internally stressed, as in element 36. In some embodiments where the haptic is stiffer than the optic, the haptic is generally relaxed and returns nearly to the size and shape it had before the external stress was applied, while the optic becomes stretched or compressed to maintain contact with the generally relaxed haptic. Note that in this generally relaxed state of the intraocular lens, the haptic may have some residual stresses that oppose the internal stresses of the optic; the magnitude of these residual stresses may vary inversely with the stiffness of the haptic. For typical haptics, which are much stiffer than the optic, the residual stresses are quite small, and the haptic may be considered to be essentially relaxed.

For the purposes of this document, an intraocular lens and/or the optic contained therein in which a haptic uses its internal stress to affect the internal stress of the optic may be referred to as a "pre-stressed" intraocular lens and/or a "pre-stressed" optic.

Figure 4:
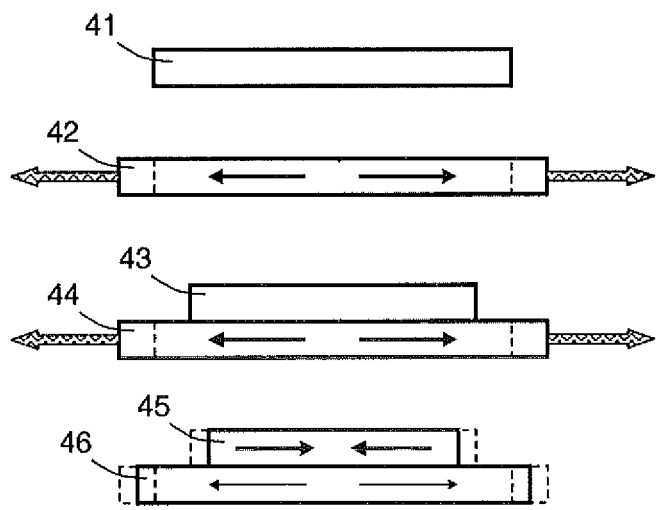
FIG. 4 is an end-on drawing of a haptic and optic, shown throughout various stages of construction.

FIG. 4 is an end-on drawing of a haptic and optic, shown throughout various stages of construction. In this figure, the optical axis is vertical and the plane of the lens is horizontal.

For the purposes of this figure and several of the following figures, the haptic is drawn as being essentially solid, and the optic is attached to the side of the haptic. It will be understood that in practice, the haptic may be hollow or cylindrical in nature, such as a circumferential ring, and may surround all or part of the optic around its equator and/or may at least partially protrude into the optic.

The topmost element 41 is a haptic in a natural, unstressed state, without an optic.

The next element down is the haptic 42 with an external stress applied. An external force, denoted by the shaded arrows at the left and right of element 42, expands the haptic. The haptic increases in size, as shown by the dotted lines that indicate the unstressed size of the haptic. The haptic also has an internal stress, denoted by the solid arrows inside the haptic. In this case, the haptic is under tension.

Still further down, an optic 43 is placed within the stressed haptic 44. Although the optic typically does not extend along the optical axis past the edges of the haptic, it is drawn as such in FIG. 4 for simplicity.

At the bottom of FIG. 4, the external force is removed from the haptic 46. The haptic 46 largely relaxes and returns nearly to its original, unstressed size, as shown by the pair of dotted lines at each end of the haptic 46. The optic 45, which is mechanically coupled to the haptic 46 and is typically less stiff than the haptic 46, provides little resistance to the change in size of the haptic. As a result, the optic 45 becomes compressed and develops an internal stress, shown by the pair of solid arrows inside the optic 45. In this case, the internal stress of the optic 45 is compression. In other embodiments, the internal stress of the optic 45 is stretched expansion.

Note that the internal stress of the haptic 46 is largely relieved by removing the external stress. However, there may be a small residual internal stress that remains inside the haptic 46, which is denoted by the thin, solid arrows inside the haptic 46. The magnitude of this residual stress may be proportional to the stiffness of the optic 45; if the optic 45 had no stiffness at all, there would be no residual stress, and the haptic 46 would be completely relaxed and would return roughly to its unstressed size.

Figure 5:
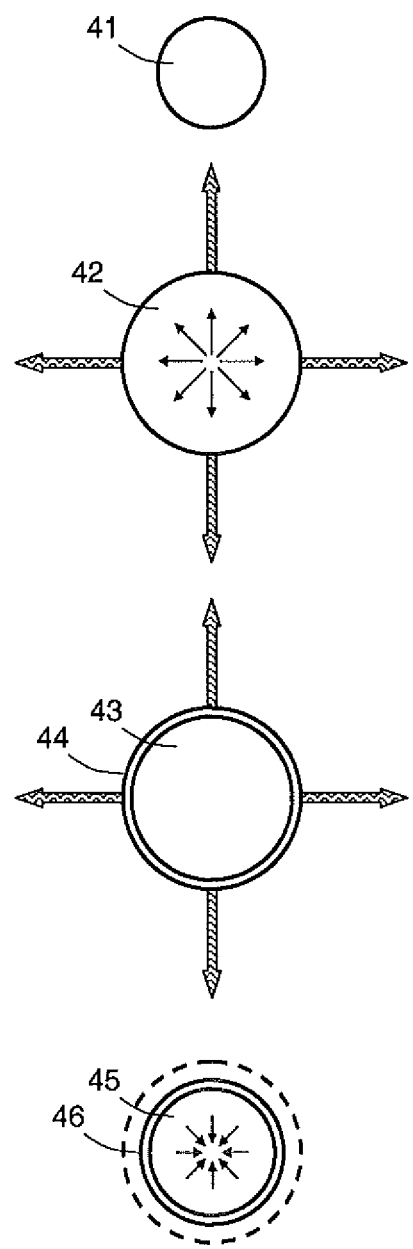
FIG. 5 is an isometric drawing of the haptic and optic of FIG. 4, only with the lens in the plane of the page and the optical axis of the lens being perpendicular to the page.

FIG. 5 shows the haptic and optic of FIG. 4, only with the lens in the plane of the page and the optical axis of the lens being perpendicular to the page.

Element 41 is the haptic in an unstressed state. For clarity, the dotted lines showing the unstressed size of the haptic are omitted.

Element 42 is the haptic with an external stress applied. In this case, the external stress is an expansion, and the haptic 42 is under tension. In some embodiments, the external stress and tension are both radially symmetric.

Element 43 is the optic, placed within the stressed haptic 44. At this stage, the optic 43 is not under significant stress.

The external stress is removed at the bottom of FIG. 5, and the haptic 46 and optic 45 are both seen to radially contract, causing an internal stress in the optic 45. In this case, the internal stress in the optic 45 is compression. At this stage, the lens may be ready for implantation.

Figure 7:
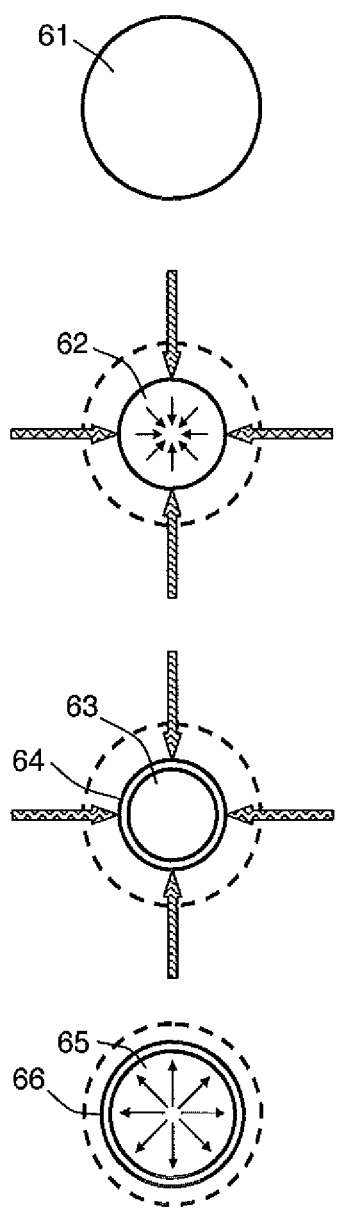
FIG. 7 is an isometric drawing of the haptic and optic of FIG. 5, only with the lens in the plane of the page and the optical axis of the lens being perpendicular to the page.

FIGS. 6 and 7 are analogous to FIGS. 4 and 5, but the external force applied to the haptic is compression rather than expansion. Note that combinations of compression and expansion are possible, with compression along one direction and expansion along another, although these are not shown in the figures.

FIG. 6 is an end-on drawing of a haptic and optic, shown throughout various stages of construction. In this figure, the optical axis is vertical and the plane of the lens is horizontal.

The topmost element 61 is haptic in a natural, unstressed state, without an optic.

The next element down is the haptic 62 with an external stress applied. An external force, denoted by the shaded arrows at the left and right of element 62, compresses the haptic. The haptic decreases in size, as shown by the dotted lines that indicate the unstressed size of the haptic. The haptic also has an internal stress, denoted by the solid arrows inside the haptic. In this case, the haptic is under compression.

Still further down, an optic 63 is placed within the stressed haptic 64. Although the optic typically does not extend along the optical axis past the edges of the haptic, it is drawn as such in FIG. 6 for simplicity.

At the bottom of FIG. 6, the external force is removed from the haptic 66. The haptic 66 largely relaxes and returns nearly to its original, unstressed size, as shown by the pair of dotted lines at each end of the haptic 66. The optic 65, which is mechanically coupled to the haptic 66 and is typically less stiff than the haptic 66, provides little resistance to the change in size of the haptic. As a result, the optic 65 becomes expanded and develops an internal stress, shown by the pair of solid arrows inside the optic 65. In this case, the internal stress of the optic 65 is tension.

FIG. 7 shows the haptic and optic of FIG. 5, only with the lens in the plane of the page and the optical axis of the lens being perpendicular to the page.

Element 61 is the haptic in an unstressed state. For clarity, the dotted lines showing the unstressed size of the haptic are omitted.

Element 62 is the haptic with an external stress applied. In this case, the external stress is a compression, and the haptic 62 is under compression. In some embodiments, the external stress and compression are both radially symmetric.

Element 63 is the optic, placed within the stressed haptic 64. At this stage, the optic 63 is not under significant stress.

The external stress is removed at the bottom of FIG. 7, and the haptic 66 and optic 65 are both seen to radially expand, causing an internal stress in the optic 65. In this case, the internal stress in the optic 65 is tension. At this stage, the lens may be ready for implantation.

FIGS. 8 and 9 show a haptic 81 and optic 82 analogous to those in the bottom portion of FIG. 7, but with an asymmetric external force applied to the haptic 81. Such an asymmetry may be used to reduce astigmatism in the optical system of an eye.

In FIG. 8, a haptic 81 is under compression from an asymmetric external force. In FIG. 8, the compressive force is larger in the vertical direction than in the horizontal direction, although in practice, the asymmetry may have any orientation and any degree of asymmetry. In addition, the asymmetry may optionally include a compressive force along one dimension and an expansive force along another. Alternatively, the asymmetry may include an expansive force along one dimension and an expansive force with a different magnitude along a different dimension.

While under the external compression, the haptic 81 is shown in FIG. 8 to be elliptical in shape, with a compressed size smaller than the uncompressed size denoted by the dashed line 83. An optic 82 is placed within the externally compressed haptic 81. At this stage, the optic 82 is largely unstressed.

Once the optic is placed within the externally stressed haptic, the external stress is removed. The haptic 91 and optic 92 then expand, as shown in FIG. 9. The resulting tension within the optic 92 may be radially asymmetric, with a direction-dependent tension that varies as a function of how much the haptic 81 was externally compressed along the particular direction. In FIG. 9, the tension along the vertical direction is larger than along the horizontal direction. Note that the asymmetry stresses in the optic 92 may have any orientation, and are not confined to vertical and horizontal, as shown in FIG. 9.

Note that in FIGS. 4 though 9, the haptic is stretched or compressed by an external force. In one embodiment, the external force is mechanical in origin, and may be realized by pushing or pulling on various locations on the haptic.

Note also that for the typical circularly symmetric geometries of an intraocular lens, the stresses in the haptic and optic are generally radial in orientation and are generally coaxial with each other.

In another embodiment, the pre-stress is caused by shrinkage or expansion of the materials during molding, extraction or another manufacturing or processing step. The haptic and the optic may be made from materials having different mechanical properties, so that during a shrinking or expanding step, one shrinks or expands more than the other. If the optic is placed within the haptic before the shrinking or expanding step, then the optic and/or haptic may become internally stressed after the shrinking or expanding step. Note that if the haptic is significantly stiffer than the optic, then the optic may have significantly more internal stress than the haptic after the shrinking or expanding step.

Figure 10:
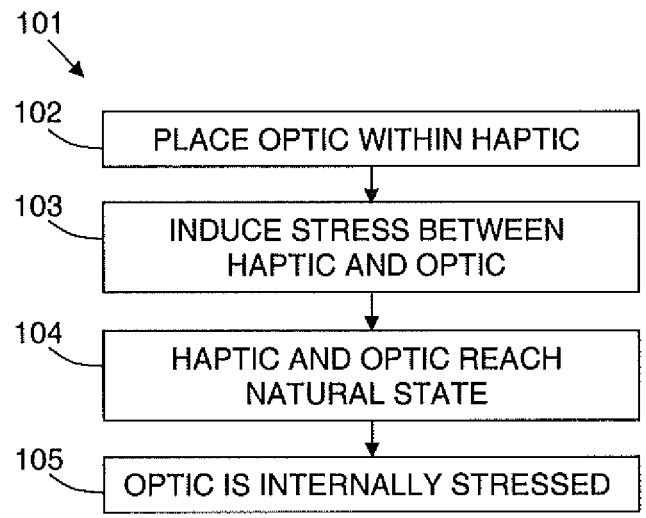
FIG. 10 is a flow chart of a manufacturing process that may induce an internal stress to the optic.

FIG. 10 is a flow chart of an exemplary manufacturing process 101 that may induce an internal stress to the optic. Initially, the haptic may be provided for the manufacturing process. In one embodiment, the haptic is externally stressed, where the external stress is to be removed at a later manufacturing step; this is analogous to the manufacturing process shown above in FIG. 3. In another embodiment, the haptic is essentially unstressed at this stage. Such an initially unstressed haptic may be made from a material that may expand or contract in response to a size-altering process, such as a heating, a cooling, or an absorption or emission of water or other substance.

In element 102, an optic is placed within the haptic. In one embodiment, the optic may be molded onto or around the haptic. In another embodiment, the optic may be manufactured separately from the haptic and then attached to the haptic. The optic may be attached to the interior of the haptic, or may be attached to the exterior of the haptic. The haptic may surround all or part of the optic, or may be adjacent to the optic. In all of these cases, the optic is said to be "placed within" the haptic.

In element 103, stress is induced between the haptic and the optic. The stress may be induced by changing the size and/or shape of the haptic and/or the optic, once the optic has been placed within the haptic. As long as the haptic and optic expand or contract by different amounts, there will be a stress between the haptic and the optic. For instance, the haptic may expand and the optic may contract, remain the same size, or expand by amount different from that of the haptic. Alternatively, the haptic may contract and the optic may expand, remain the same size, or contract by amount different from that of the haptic. As a further alternative, the haptic may remain the same size and the optic may contract or expand.

Because the haptic and the optic may be connected after element 102 in FIG. 10, the haptic and optic may not be able to expand or contract free of each other. For instance, if the haptic surrounds the optic so that the outer diameter of the optic fits inside the inner diameter of the haptic, the optic may not expand significantly compared to what its expansion would be if it were not mounted within the haptic. In this case, an expansion of the optic by heating or another method may not produce a significant expansion of the optic, but may produce compression within the optic. For this reason, the expansion and/or contraction described above may be considered to be an expansion and/or contraction in free space, as if the haptic were detached from the optic.

In element 104, the haptic and the optic reach a natural state, analogous to element 35 in FIG. 3. In element 105, the optic is internally stressed, analogous to element 36 in FIG. 3.

In one embodiment, the expansion and/or contraction may be caused by a shrinking and/or expanding step that occurs during molding, extraction or any other manufacturing or processing step. For instance, if the haptic has a higher shrinkage than the optic, and the optic is placed within the haptic before a shrinking step, then the optic may be in a compressed state after the shrinking step. Similarly, if the haptic has a lower shrinkage than the optic, and the optic is placed within the haptic before a shrinking step, then the optic may be in an expanded state after the shrinking step.

In another embodiment, the pre-stress is caused by using hydrophilic and/or hydrophobic materials for the haptic and/or optic. Upon insertion into the aqueous solution of the eye, a hydrophilic material may swell and a hydrophobic material may shrink or remain the same size. The swelling and/or shrinking upon insertion into the eye is analogous to the expanding and/or shrinking steps described above.

For instance, consider a hydrophilic optic placed within a hydrophobic haptic. Upon insertion into the aqueous solution of the eye, the optic may swell and the haptic may absorb some of the swelling force. The lens may then reach an equilibrium in the eye, in which the optic may be under compression.

In one embodiment, the haptic and optic may have different levels of hydrophilia and/or hydrophobia, so that upon insertion into the eye they may swell at different rates and may therefore internally stress the optic.

As noted in FIGS. 8 and 9, the haptic may be pre-stressed differently in different directions. In addition, the haptic may also have an axial component to the pre-stressing. This axial component may help dampen or eliminate any undesirable axial movement of the lens during accommodation.

Because FIGS. 4 though 9 are largely schematic in nature, it is instructive to consider a haptic having a more realistic design.

Figure 11:
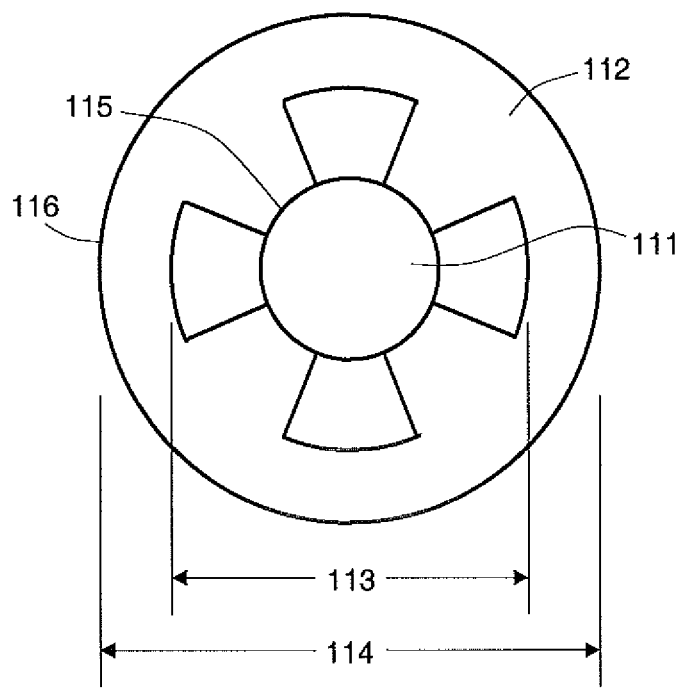
FIG. 11 is an isometric drawing of an optic placed within a haptic.

FIG. 11 is an isometric drawing of an exemplary haptic, after manufacture and prior to installation in the eye. The optic, when placed within the haptic, will be located at or near the center of the haptic. The haptic may protrude into the optic. Alternatively, the haptic may engage all or a portion of the periphery of the optic only. The outer circumference of the haptic mechanically couples with the capsular bag of the eye (not shown), so that any compression or expansion initiated by the zonules is coupled into the haptic, and, in turn, into the optic through its periphery.

The exemplary haptic has various segments or filaments, each of which extends generally radially in a plane roughly perpendicular to the optical axis of the lens. For the exemplary haptic of FIG. 11, the segments are joined to each other at the outer circumference and extend radially inward until they contact the edge of the optic. Alternatively, they need not be joined together at the outer circumference. At locations other than the outer circumference, the haptic segments may remain separate from each other, as shown in FIG. 11, or alternatively some or all segments may be joined together. Any or all of the width, shape and thickness of the segments may optionally vary along the length of the segments. The haptic may have any suitable number of segments, including but not limited to, 3, 4, 6, 8, 10, 12, 14, and 16.

The exemplary haptic 110 is then compressed radially, so that the overall diameter of the haptic is reduced. A typical compression may be on the order of about 1 mm, although more or less compression may be used. For instance, the haptic may be compressed by a fraction of its diameter, such as a value in the range of about 0.4% to about 2.0%. This compressed state may be referred to as a "pre-stressed" state.

FIG. 11 is an isometric drawing of an optic 111 placed within a haptic 112. The haptic 112 engages a portion of the periphery of the optic 111 in a region roughly around the equator 115 of the optic 111. This exemplary haptic 112 contacts the optic 111 in four regions, each roughly equally spaced apart around the equator 115 of the optic 111, although any suitable number of contact portions may be used and they need not be spaced equally apart. The haptic 112 includes an annular ring, also known as a circumferential ring. The ring has an inner diameter given by element 113, and an outer diameter given by element 114. The ratio of the inner to out diameters may vary as a function of the stiffness of the haptic 112. For instance, a stiffer haptic may require relatively little material, and the ratio may be fairly close to 1. Alternatively, a less stiff haptic may require more material, and the ratio may deviate significantly from 1.

For the haptic shown in FIG. 11, the outer diameter 116 of the annular ring is the outer portion of the haptic 112, and may remain in contact with the capsular bag of the eye during and after implantation. Alternatively, the annular ring may be contained in the interior of the haptic, with arms or filaments that may extend outward beyond the outer diameter of the annular ring to contact the capsular bag; these filaments are analogous to the four inward-extending filaments shown in FIG. 11. As a further alternative, the inner diameter of the annular ring may be the inner diameter of the haptic, and may contact the circumference or the equator of the optic.

Figure 12:
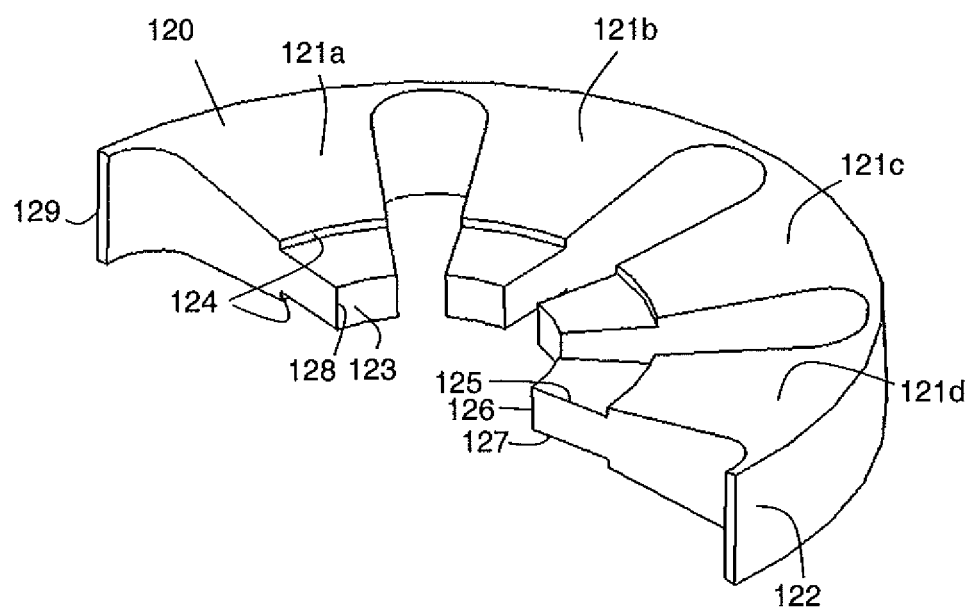
FIG. 12 is a cross-section drawing of a haptic.
Figure 13:
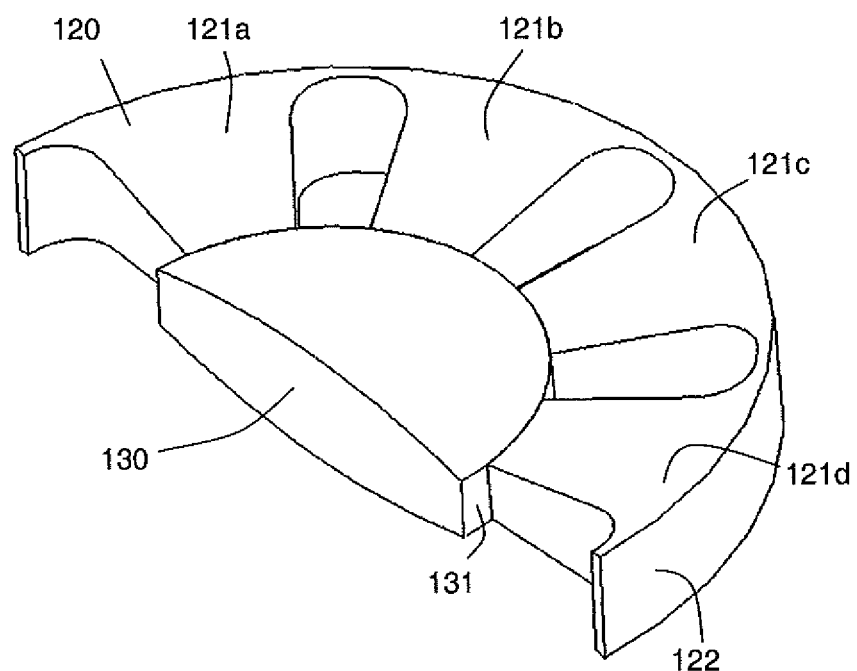
FIG. 13 is a cross-sectional drawing of the haptic of FIG. 12, with an optic.
Figure 14:
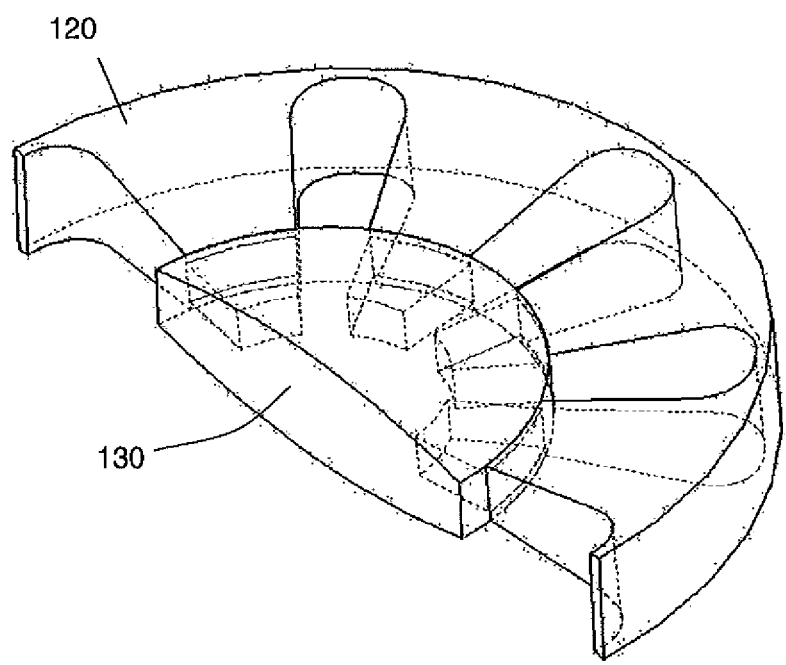
FIG. 14 is the cross-section drawing of the haptic and optic of FIG. 13, with additional hidden lines.
Figure 15:
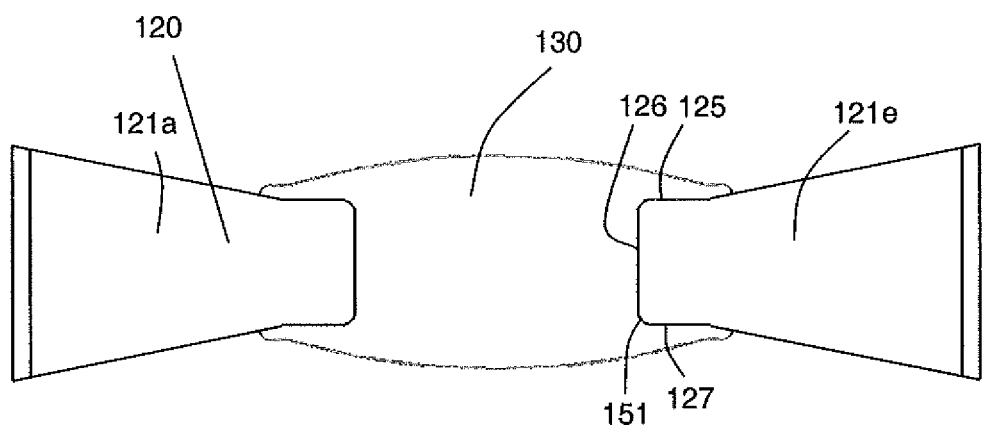
FIG. 15 is an end-on cross-sectional drawing of the haptic and optic of FIG. 13.
Figure 16:
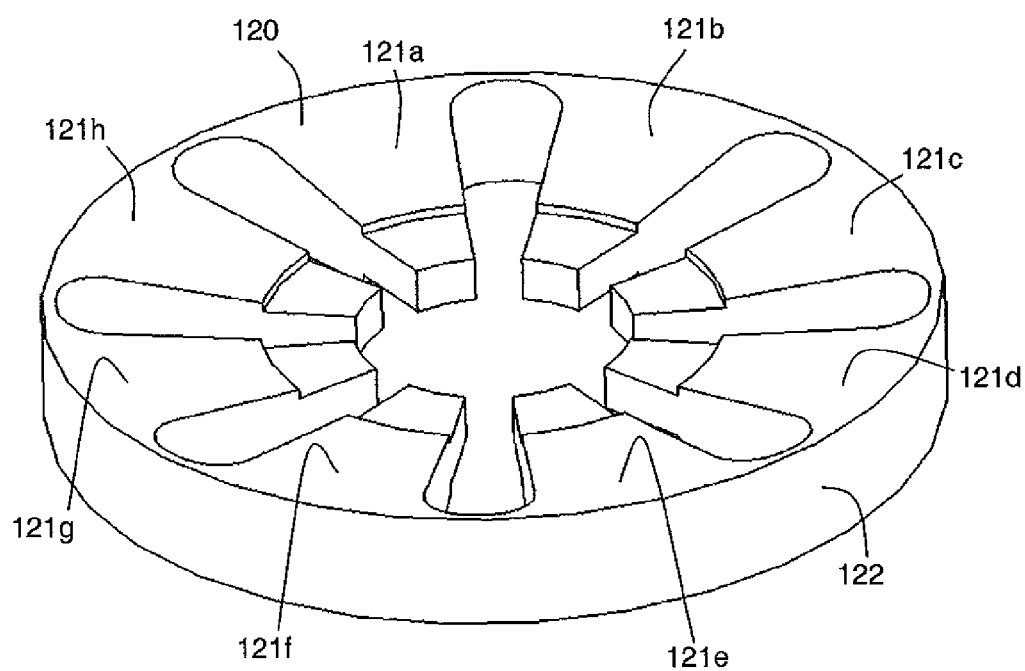
FIG. 16 is a plan drawing of the haptic of FIG. 12.
Figure 17:
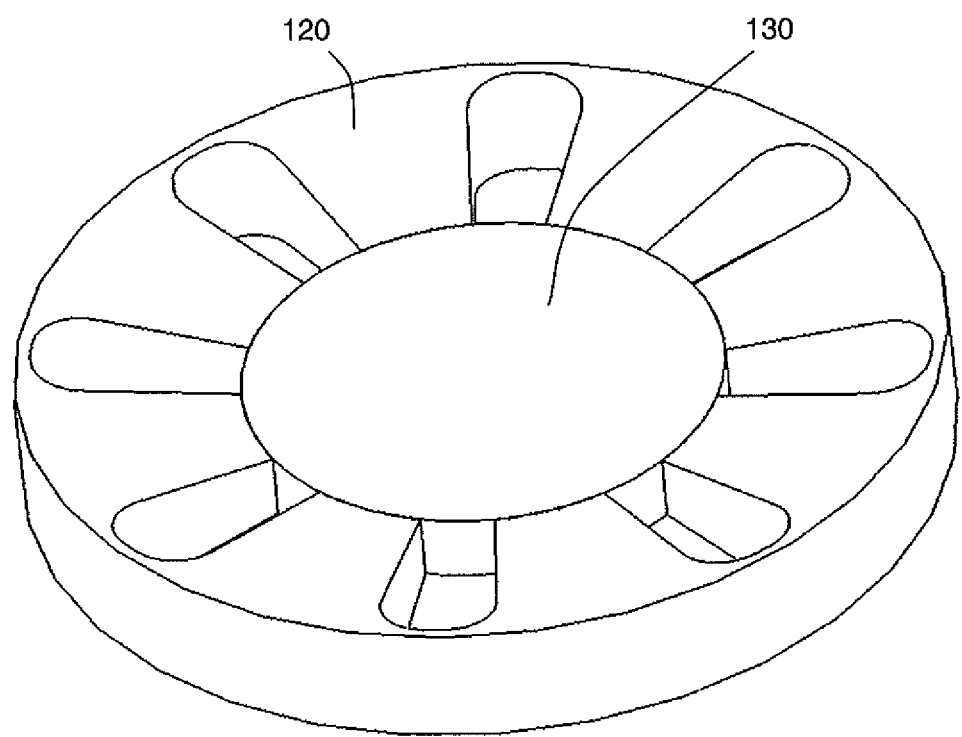
FIG. 17 is a plan drawing of the haptic of FIG. 16, with an optic.
Figure 18:
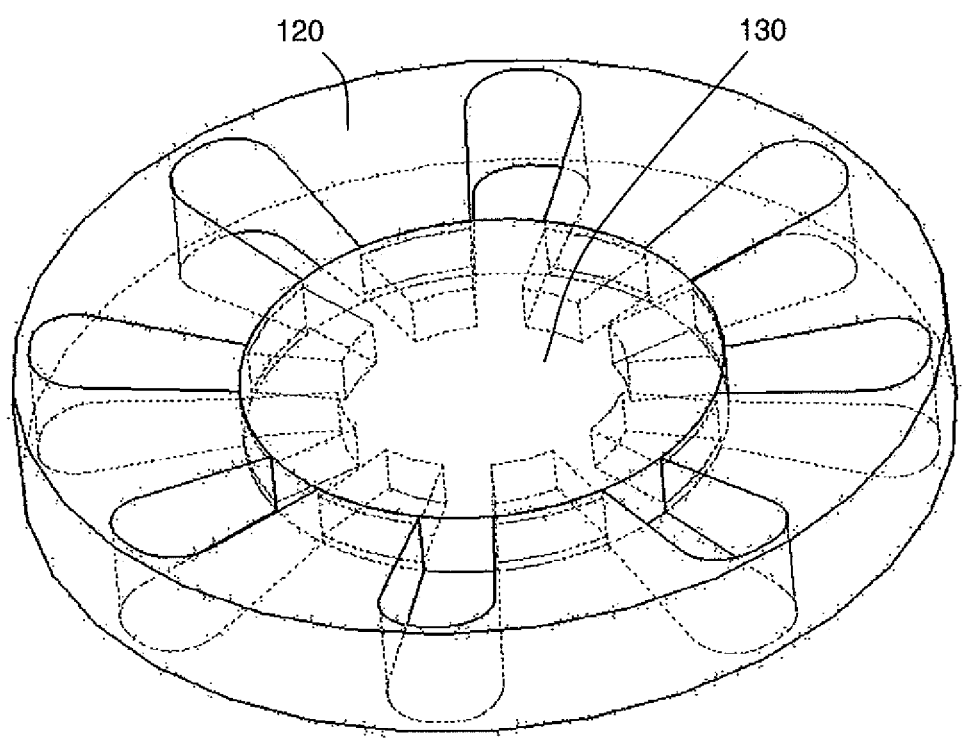
FIG. 18 is the cross-section drawing of the haptic and optic of FIG. 17, with additional hidden lines.

FIGS. 12 through 18 show an exemplary haptic 120 in various plan and cross-sectional views, both with and without an optic 130. FIG. 12 is a cross-section drawing of a haptic 120. FIG. 13 is a cross-sectional drawing of the haptic of FIG. 12, with an optic 130. FIG. 14 is the cross-section drawing of the haptic 120 and optic 130 of FIG. 13, with additional hidden lines. FIG. 15 is an end-on cross-sectional drawing of the haptic 120 and optic 130 of FIG. 13. FIG. 16 is a plan drawing of the haptic 120 of FIG. 12. FIG. 17 is a plan drawing of the haptic 120 of FIG. 16, with an optic 130. FIG. 18 is the cross-section drawing of the haptic 120 and optic 130 of FIG. 17, with additional hidden lines.

The haptic 120 of FIGS. 12 through 18 has eight filaments denoted by elements 121a through 121h. Alternatively, the haptic 120 may have more or fewer than eight filaments. The filaments 121a-h may be connected at their outermost edge and may be unconnected at their innermost edge.

Note that the filaments 121a-h may vary in size along their lengths, from the innermost edge 123 to the ends of the filament adjacent to the outermost edge 122 of the haptic 120. In particular, the filaments 121a-h may increase in cross-sectional dimensions with radial distance away from the center of the lens. In a direction parallel to the optical axis (vertical in FIG. 12), the outermost extent of the haptic filaments, denoted by length 129, may be larger than the innermost extent of the haptic filaments, denoted by dimension 128. Alternatively, the length 129 may be equal to or less than length 128. Similarly, in a direction perpendicular to the optical axis (essentially in the plane of the lens), the filaments may be effectively wedge-shaped, with a greater radial extent at the outer edge than at the inner edge. The cross-section of each filament may be symmetric with respect to the plane of the lens, as shown in FIG. 12. Alternatively, the cross-section of one or more filaments may be asymmetric with respect to the plane of the lens, with differing amounts of material on anterior and posterior sides of the filament.

The outermost edge 122 of the haptic 120 mechanically couples the intraocular lens to the capsular bag of the eye. The haptic 120 may receive an optic 130 in its central region, which may be molded directly onto the haptic 120. Alternatively, the optic may be manufactured separately from the haptic, then attached to the haptic.

The haptic 120 may have an optional lip or ridge 124 on one or both of the anterior and posterior faces, so that if an optic is molded directly onto the haptic 120, the optic resides in the central portion of the haptic within the lip 124. The lip 124 may be circularly symmetric on both faces of the haptic, as shown in FIGS. 12 through 18. Alternatively, the lip 124 may have a different radius on one or more filaments, so that optic material may extend out different radial distances along particular filaments. As a further alternative, the lip 124 may have different radii on the anterior and posterior faces of the haptic 120.

Once the optic 130 is formed on, attached to, or placed within the haptic 120, the haptic 120 protrudes into the edge 131 of the optic 130. For the specific design of FIGS. 12 through 18, portions of each filament 121a-h extend into the edge 131 of the optic 130, with the anterior and posterior faces of the optic 130 surrounding and/or encompassing the haptic filaments 121a-h in the central portion demarcated by the lip 124.

For a cross-section of the filaments 121 a-h, taken in a plane parallel to the optical axis of the lens (vertical in FIGS. 12 through 18), the cross-section has a particular profile that extends into the edge 131 of the optic 130. The profile may contain one or more straight and/or curved portions, and may have a deepest portion at one or more points or along a straight segment. For instance, the profile in FIGS. 12 and 15 has a generally straight portion 125 extending generally radially inward, followed by a generally straight portion 126 extending generally parallel to the optical axis, followed by a generally straight portion 127 extending generally radially outward. The generally straight portions 125, 126 and 127 may optionally have one or more rounded portions 151 between them. Straight portions 125 and 127 may be generally parallel to each other, or may be generally inclined with respect to each other. The generally straight portion 126 may be generally parallel to the optical axis, as in FIGS. 12 and 15, or may alternatively be inclined with respect to the optical axis. The deepest portion of the profile of FIGS. 12 and 15 may be the straight portion 126. The profile made up of segments 125, 126 and 127 shown in FIGS. 12 and 15 may be generally convex in a direction parallel to the optical axis of the lens. Other configurations of protruding haptics may incorporated into embodiments of the present invention such, for examples, those discussed in copending U.S. patent application Ser. No. 11/618,325, which is herein incorporated by reference.

Referring to FIG. 15, the axial thickness (i.e., along an axis parallel to the optical axis passing through the center of the optic 130) of the portions of the haptic 120 disposed within the optic 130 may be selected to control the amount and/or distribution of an ocular force acting on the intraocular lens 240. For example, in some embodiments, the performance (e.g., the change Diopter power of the optic 130 between accommodative and disaccommodative configurations) increases as the edge thickness increases. In such embodiments, other design constraints (e.g., optical performance or physical constraints of the eye) may, however, place an upper limit on the maximum optic edge thickness. In some embodiments, the portion of the haptic 120 inside the optic 130 has a maximum axial thickness that is at least one half a maximum axial thickness of the optic 130 along the optical axis, as clearly illustrated in FIG. 15. In other embodiments, the portion of the haptic 120 inside the optic 130 has a maximum axial thickness that is at least 75% of a maximum axial thickness of the central zone. The advantages of the axial thickness the protruding portions of the haptic 120 may also be applied to other embodiments of the invention discussed herein.

In certain embodiments, the optic 130 is a multifocal optic. For example, the portion of the optic 130 between the ends 126 of the haptic 120 may comprise a first zone having a first optical power and the portion of the optic 130 into which the filaments 121 protrude may comprise a second zone having a second optic power that is different from the first optical power. In some embodiments, the optic 130 may change from a monofocal optic to a multifocal optic, depending upon the amount of ocular force on the haptic 120 and/or the state of accommodation of the eye into which the intraocular lens is inserted.

If the optic 130 may be molded directly onto the haptic 120, the haptic 120 may be first expanded or contracted radially by an external force, prior to molding. The optic 130 may then be molded directly onto the expanded or contracted haptic 120. After molding, the external force may be removed, and the haptic may return to its original size or fairly close to its original size, forming radial stresses within the optic 130.

It is desirable that the haptic be made from a stiffer material than the optic, so that any distorting forces induced by the zonules or capsular bag are transmitted efficiently through the haptic to the optic, and efficiently change the shape of the optic. It is also desirable that the haptic and the optic have similar or essentially equal refractive indices, which would reduce any reflections at the interfaces between the haptic and the optic.

Figure 19:
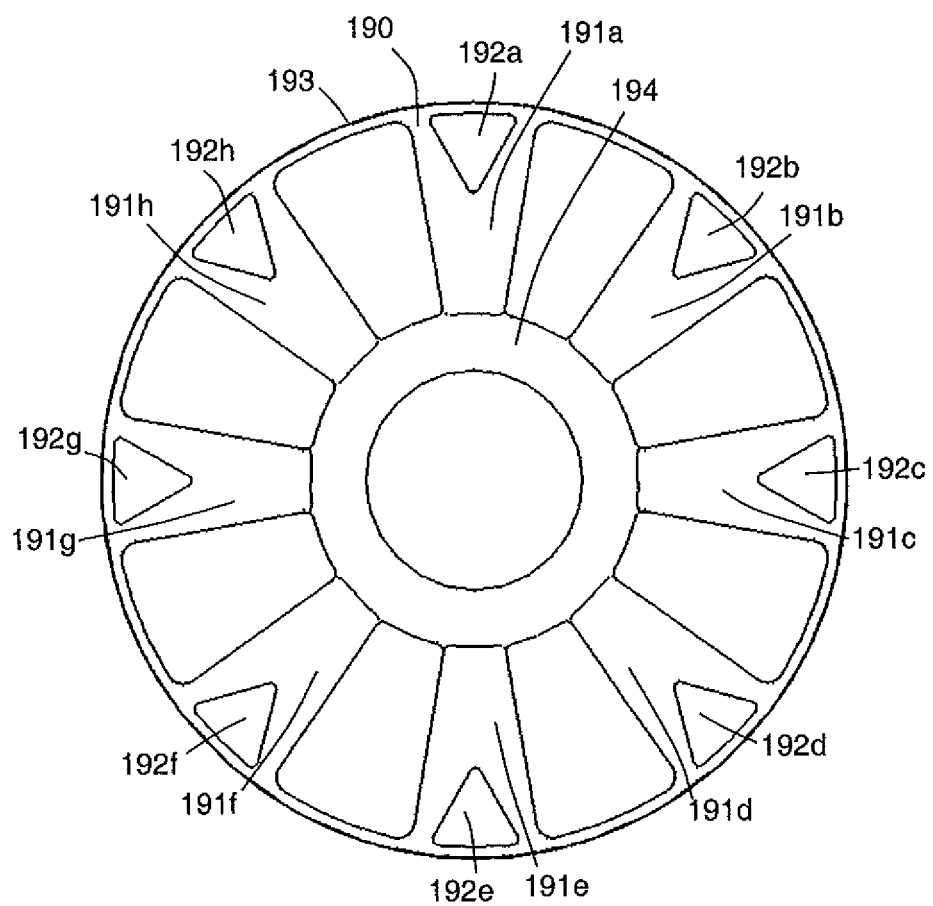
FIG. 19 is a plan drawing of a haptic.
Figure 20:
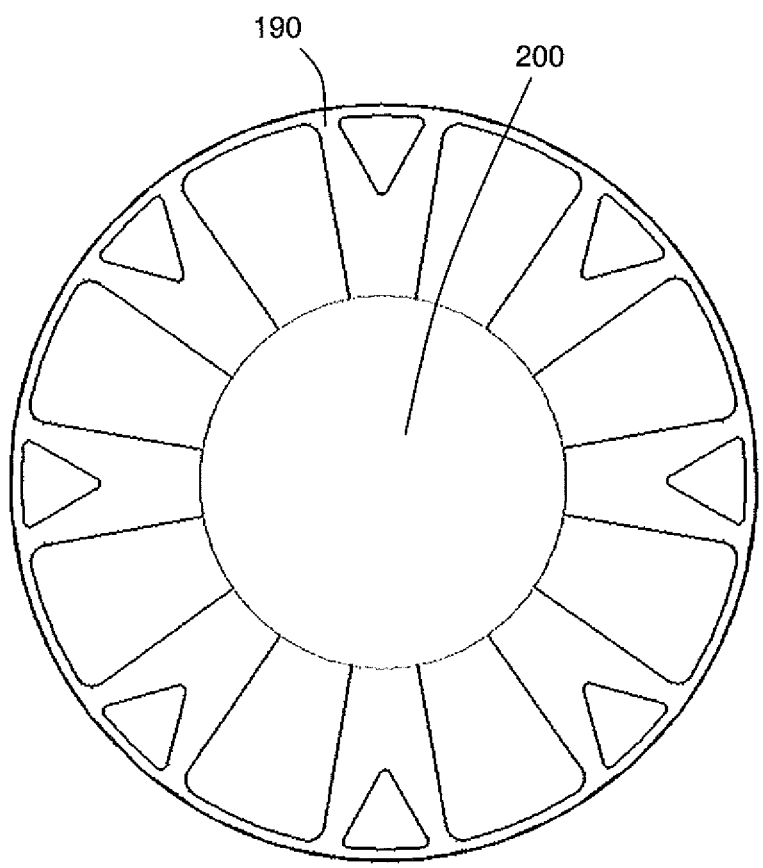
FIG. 20 is a plan drawing of the haptic of FIG. 19, with an optic.
Figure 21:
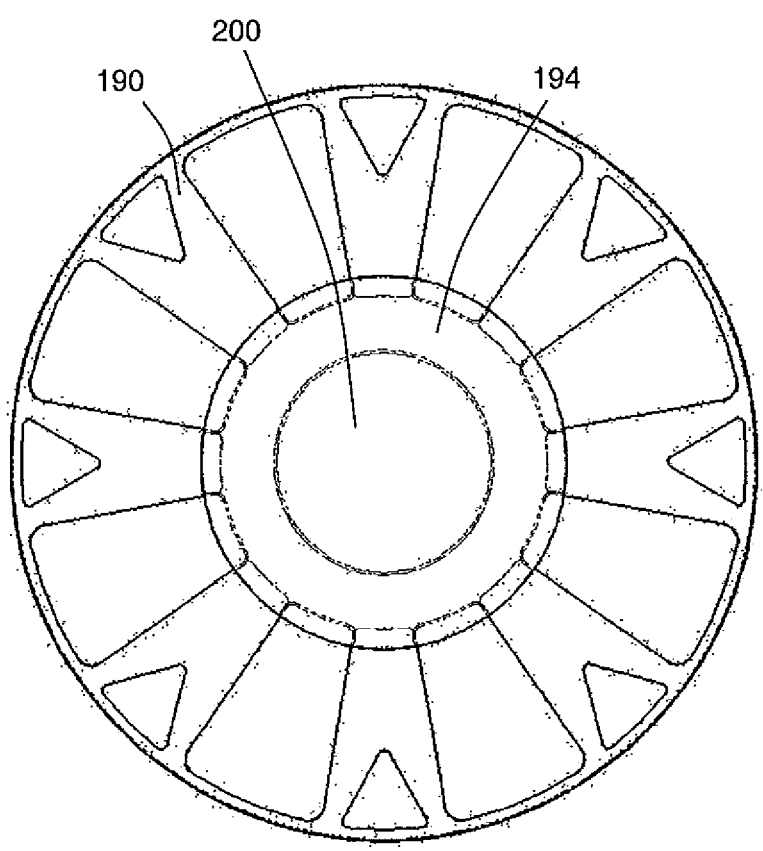
FIG. 21 is the plan drawing of the haptic and optic of FIG. 20, with additional hidden lines.

FIGS. 19 through 21 show another exemplary haptic 190 in various plan views, both with and without an optic 200. FIG. 19 is a plan drawing of a haptic 190. FIG. 20 is a plan drawing of the haptic 190 of FIG. 19, with an optic 200. FIG. 21 is the plan drawing of the haptic 190 and optic 200 of FIG. 20, with additional hidden lines.

The haptic 190 of FIGS. 19 through 21 has eight filaments denoted by elements 191a through 191h. Alternatively, the haptic 190 may have more or fewer than eight filaments. Filaments 191 a-h may have non-uniformities along their lengths, such as width variations, height variations, and/or holes 192a-h.

The holes 192a-h may desirably alter the mechanical properties of the respective filaments, so that a given zonular force may be transmitted efficiently into a distortion of the optic. The holes 192a-h may be triangular in shape, or may be any other suitable shape, such as round, square, rectangular, polygonal, and may optionally have one or more rounded corners and/or edges. Each hole may optionally vary in profile along its depth. There may optionally be more than one hole per filament. There may optionally be differing numbers of holes for different filaments. There may optionally be differently-shaped holes on the same filament.

Unlike the filaments 121 a-h of FIGS. 12 through 18, the filaments 191 a-h are connected at both their outermost edge and their innermost edge. The filaments 191a-h are joined at an outer annular ring 193 and an inner annular ring 194. The inner annular ring 194 along with a portion of the filaments in proximity thereto may lie within the circumference of the optic 200, as in FIGS. 19 through 21. Alternatively, the inner annular ring 194 may lie outside the circumference of the optic 200, or may straddle the circumference of the optic 200.

The dimensions of the inner annular ring 194, specifically, the inner and outer diameters of the inner annular ring 194, may be determined in part by the stiffness of the haptic 190 and/or the stiffness of the optic 200. For instance, a stiffer haptic may require relatively little material, and the ratio may be fairly close to 1. Alternatively, a less stiff haptic may require more material, and the ratio may deviate significantly from 1.

Figure 22:
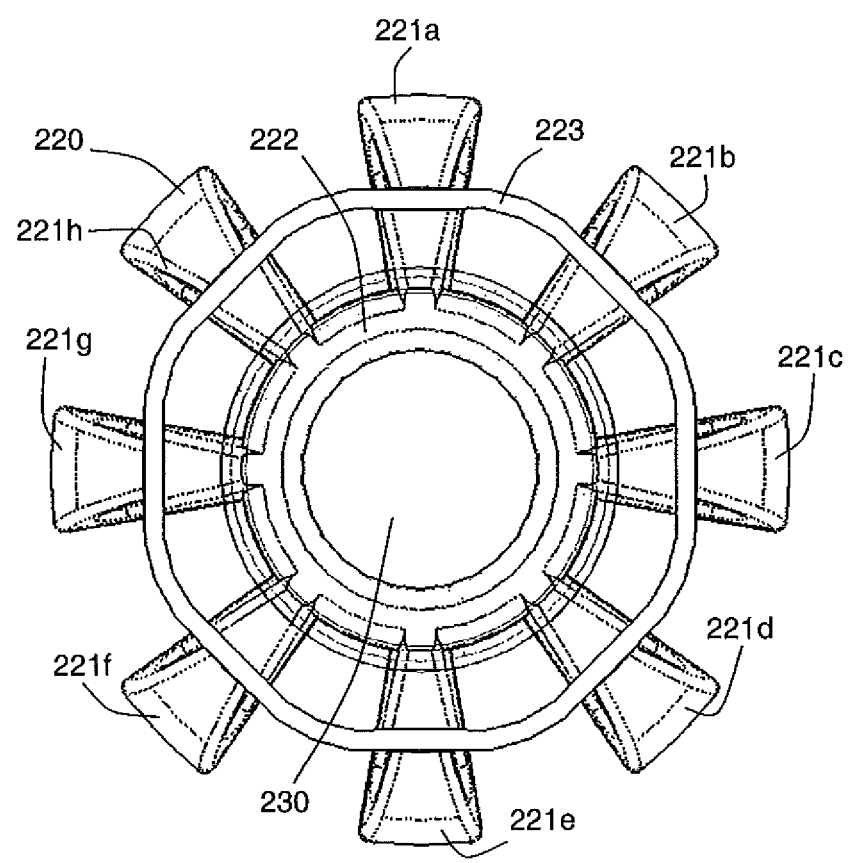
FIG. 22 is a top-view plan drawing of a haptic with an optic.
Figure 23:
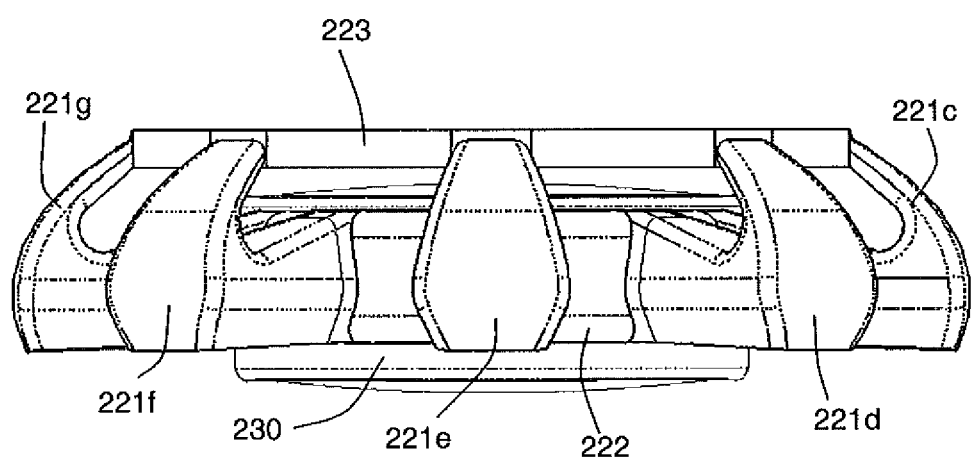
FIG. 23 is a side-view plan drawing of the haptic and optic of FIG. 22.
Figure 24:
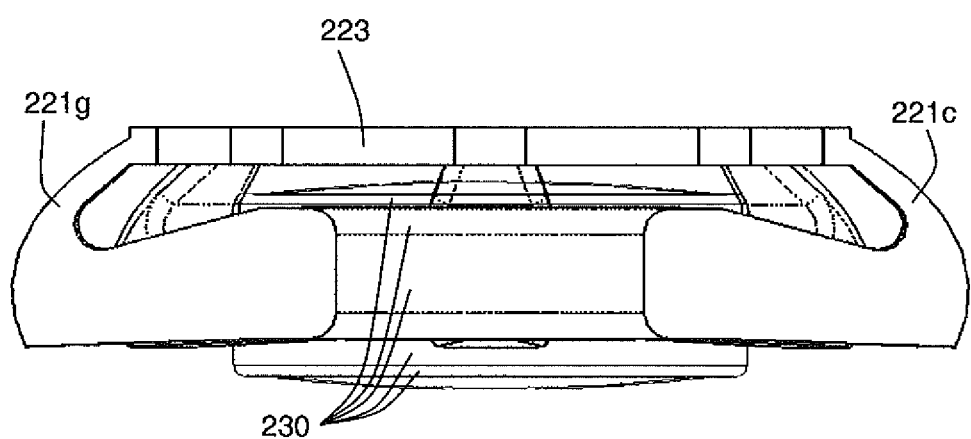
FIG. 24 is a side-view cross-sectional drawing of the haptic and optic of FIG. 22.
Figure 25:
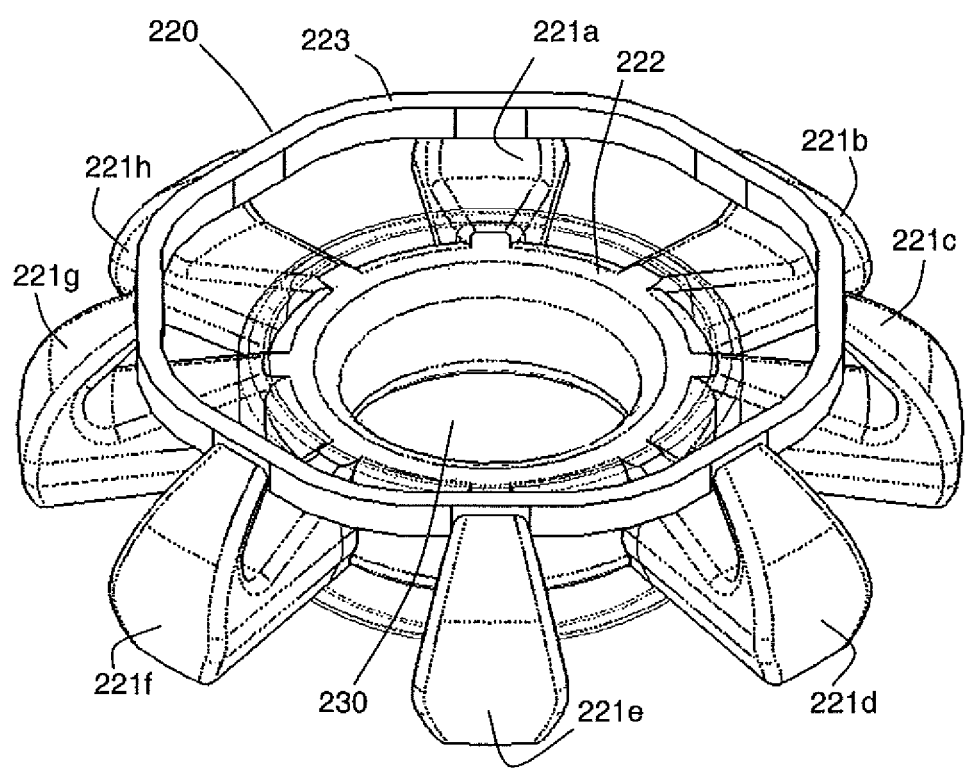
FIG. 25 is a plan drawing of the haptic and optic of FIG. 22.
Figure 26:
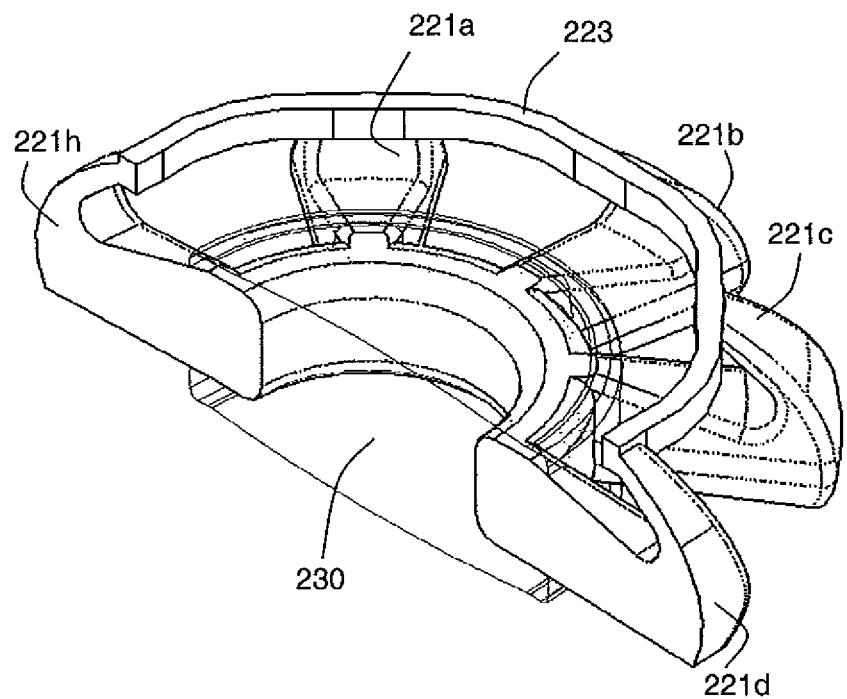
FIG. 26 is a cross-sectional drawing of the haptic and optic of FIG. 22.

FIGS. 22 through 26 show another exemplary haptic 220 in various plan views, with an optic 230. FIG. 22 is a top-view plan drawing of a haptic 220 with an optic 230. FIG. 23 is a side-view plan drawing of the haptic 220 and optic 230 of FIG. 22. FIG. 24 is a side-view cross-sectional drawing of the haptic 220 and optic 230 of FIG. 22. FIG. 25 is a plan drawing of the haptic 220 and optic 230 of FIG. 22. FIG. 26 is a cross-sectional drawing of the haptic 220 and optic 230 of FIG. 22.

The haptic 220 of FIGS. 22 through 26 has a more complex shape than the haptics shown in FIGS. 12 through 21. The haptic 220 has eight filaments 221 a-h, each of which has one end attached to an inner annular ring 222 and has the opposite end attached to an outer annular ring 223. Alternatively, the haptic 220 may have more or fewer than eight filaments. In contrast with the haptics of FIGS. 12 through 21, the haptic 220 contacts the capsular bag of the eye at one or more points along the filaments 221 a-h between the inner and outer annular rings 222 and 223. In some embodiments, the filaments 221 a-h may loop back on themselves, and may contact the capsular bag at one or more extrema along the loop, rather than at the outer annular ring 223.

As with the inner annular ring 194 of FIGS. 19 through 21, the inner annular ring 222 may lie inside the circumference of the optic 230, once the optic 230 is placed within the haptic 220, may lie outside the circumference of the optic 230, or may straddle the circumference of the optic 230.

In some embodiments, such as the disc-shaped intraocular lenses shown in FIGS. 12 through 21, the haptic filaments engage an equatorial region of the capsular bag. In many of these embodiments, the optical power of intraocular lens may be selected to provide a disaccommodative bias, although some embodiments may alternatively provide an accommodative bias.

In other embodiments, the haptic filaments may engage substantially the entire capsular bag, rather than just the equatorial region of the capsular bag. In some of these embodiments, the filaments may extend generally in a plane that includes the optical axis of the lens, and there may be uncontacted portions of the capsular bag in the regions between the filaments. In many of these embodiments, the intraocular lens has an accommodative bias, although some embodiments may alternatively use a disaccommodative bias.

For the designs of FIGS. 12 through 26, the haptic may be pre-stressed, and the optic may then be molded onto or attached to the haptic while the haptic is in the pre-stressed state. For instance, the haptic may be compressed or expanded radially prior to placing the optic within the haptic. The pre-stress may then be removed, and the lens may be allowed to relax to its substantially unstressed state, or a "natural" state. For a haptic that is much stiffer than the optic, the haptic may expand/contract by nearly the full compression/expansion amount, and the optic becomes expanded/compressed about its equator. In its expanded state, the optic is under radial tension.

This pre-stress may help reduce or eliminate buckling of the optic, if the optic is compressed. It may also reduce the need for a thicker optic for maximizing the power change for a given external force (e.g., an ocular force produced by the ciliary muscles, the zonules, and/or the capsular bag of the eye.) Furthermore, the pre-stress may allow for a so-called "fail-safe" design that allows only a certain amount of power change during accommodation; the lens may minimize the power change beyond a prescribed accommodation range. In addition, the pre-stress may reduce the amount of force required for a given power change.

The optic may be made from a relatively soft material, so that it can distort or change shape readily under the limited deforming force initiated by the capsular bag and transmitted through the haptic. An exemplary material is a relatively soft silicone material, although other suitable materials may be used as well. The stiffness of the optic 121 may be less than 500 kPa, or preferably may be between 0.5 kPa and 500 kPa, or more preferably may be between 25 kPa and 200 kPa, or even more preferably may be between 25 kPa and 50 kPa.

In contrast with the optic, the haptic may be made from a relatively stiff material, so that it can efficiently transmit the deforming forces from the capsular bag to the optic. An exemplary material is a relatively stiff silicone material, although other suitable materials may be used as well, such as acrylic, polystyrene, or clear polyurethanes. The haptic may preferably be stiffer than the optic. The stiffness of the haptic may be greater than 500 kPa, or preferably may be greater than 3000 kPa.

Because the haptic may extend into the optic in a region around its circumference, it also may extend into the clear aperture of the optic. For this reason, the haptic may preferably be transparent or nearly transparent, so that it does not substantially block any light transmitted through the lens. The haptic generally has a power transmission of at least about 80%, preferably at least 90% or even 95%.

In addition, it is desirable that the interface between the optic and the haptic not produce any significant reflections, which would produce scattered light within the eye, and would appear as a haze to the patient. A convenient way to reduce the reflections from the interface is to match the refractive indices of the haptic and the optic to each other.

A simple numerical example shows the effect of mismatch of refractive indices on reflected power. For a planar interface at normal incidence between air (refractive index of 1) and glass (refractive index of 1.5), 4% of the incident power is reflected at the interface. For such an interface between air and glass, there is no attempt to match refractive indices, and this 4% reflection will merely provide a baseline for comparison. If, instead of 1 and 1.5, the refractive indices differ by 4%, such as 1.5 and 1.56 or 1.5 and 1.44, there is a 0.04% reflection, or a factor of 100 improvement over air/glass. Finally, if the refractive indices differ by only 0.3%, such as 1.5 and 1.505 or 1.5 and 1.495, there is a 0.00028% reflection, or a factor of over 14000 improvement over air/glass. In practice, tolerances such as the 0.3% case may be achievable, and it is seen that a negligible fraction of power may be reflected at the interface between a haptic and an optic whose refractive indices differ by 0.3%. Note that the above base value of 1.5 was chosen for simplicity, and that the haptic and optic may have any suitable refractive index.

It is desirable that the refractive indices of the haptic and optic be essentially the same. For the purposes of this document, "essentially the same" may mean that their refractive indices are equal to each other at a wavelength within the visible spectrum (i.e., between 400 nm and 700 nm). Note that the haptic and optic may optionally have different dispersions, where the refractive index variation, as a function of wavelength, may be different for the haptic and the optic. In other words, if the refractive indices of the haptic and optic are plotted as a function of wavelength, they may or may not have different slopes, and if the two curves cross at one or more wavelengths between 400 nm and 700 nm, then the refractive indices may be considered to be essentially the same or essentially equal.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A deformable accommodating intraocular lens for implantation into a capsular bag of an eye, comprising:
   a deformable optic with a stiffness between 25 kPa and 200 kPa, the optic comprising an anterior face, an opposing posterior face, and a circumference around a perimeter of the optic; and
   a haptic having a stiffness greater than 500 kPa and comprising a plurality of filaments with an innermost edge and an outermost edge, wherein the plurality of filaments are connected at their outermost edge by an outer annular ring configured to engage the capsular bag and wherein the plurality of filaments are connected at their innermost edge by an inner annular ring, wherein a portion of the filaments in proximity to the innermost edge and the inner annular ring lie within the circumference of the optic, and wherein the haptic is configured to deform the optic in response to radial forces imparted on the capsular bag to provide for an increase in power of the optic so as to provide an accommodation range of at least 2 diopters;
   wherein the optic refractive index is essentially equal to the haptic refractive index, and wherein the haptic stresses the optic when the intraocular lens is in a natural state such that the internal stress is present throughout the accommodation range in order to prevent ripples and/or waves in the optic.

2. The intraocular lens of claim 1, wherein the haptic is capable of essentially filling the capsular bag of the eye.

3. The intraocular lens of claim 1, wherein the optic is disaccommodatively biased.

4. The intraocular lens of claim 1, wherein the optic and haptic are both transparent.

5. The intraocular lens of claim 1, wherein the power changes from a power of distant vision to a power of near vision in response to the radial forces.

6. The intraocular lens of claim 1, wherein the haptic stresses the optic along a radial direction when the intraocular lens is in a natural state.

7. The intraocular lens of claim 1, wherein the increase in optical power is about 3 to 4 diopters.

8. The intraocular lens of claim 1, wherein the plurality of filaments comprise at least eight filaments.

* * * * *